United States Patent
Chen et al.

(10) Patent No.: US 10,210,741 B2
(45) Date of Patent: Feb. 19, 2019

(54) FALL-OFF DETECTION METHOD FOR WEARABLE DEVICE AND WEARABLE DEVICE

(71) Applicant: Huawei Technologies Co., Ltd., Shenzhen (CN)

(72) Inventors: Wenjuan Chen, Shenzhen (CN); Yu Zhu, Shenzhen (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 0 days.

(21) Appl. No.: 15/516,540

(22) PCT Filed: Oct. 15, 2014

(86) PCT No.: PCT/CN2014/088665
§ 371 (c)(1),
(2) Date: Apr. 3, 2017

(87) PCT Pub. No.: WO2016/058145
PCT Pub. Date: Apr. 21, 2016

(65) Prior Publication Data
US 2017/0301214 A1 Oct. 19, 2017

(51) Int. Cl.
*G08B 1/00* (2006.01)
*G08B 21/24* (2006.01)
(Continued)

(52) U.S. Cl.
CPC ............ *G08B 21/24* (2013.01); *A61B 5/0024* (2013.01); *A61B 5/01* (2013.01); *A61B 5/0404* (2013.01);
(Continued)

(58) Field of Classification Search
CPC .... G08B 21/24; G08B 21/043; A61B 5/0024; H04W 4/027; H04W 88/02
(Continued)

(56) References Cited

U.S. PATENT DOCUMENTS

| 8,410,926 | B1 | 4/2013 | Gary, Jr. et al. |
| 9,231,765 | B2 * | 1/2016 | Flautner ............... H04L 9/3226 |
| 2009/0264714 | A1 | 10/2009 | Chou |

FOREIGN PATENT DOCUMENTS

| CN | 101073494 A | 11/2007 |
| CN | 203504628 U | 3/2014 |

(Continued)

OTHER PUBLICATIONS

Machine Translation and Abstract of Chinese Publication No. CN103997713, Aug. 20, 2014, 9 pages.
(Continued)

*Primary Examiner* — Daryl Pope
(74) *Attorney, Agent, or Firm* — Conley Rose, P.C.

(57) ABSTRACT

Embodiments of the present disclosure disclose a fall-off detection method for a wearable device and a wearable device. The method includes collecting physiological parameter information and activity information of a wearer of the wearable device; when an abnormality is detected in the physiological parameter information of the wearer of the wearable device and a time of the abnormality exceeds a preset time, determining that the wearable device falls off from the wearer; when it is determined that the wearable device falls off from the wearer, determining, according to the collected physiological parameter information and activity information of the wearer of the wearable device, a scenario mode that the wearer is in; and sending, according to the scenario mode that the wearer is in, an indication corresponding to the scenario mode.

14 Claims, 9 Drawing Sheets

(51) Int. Cl.
| | |
|---|---|
| *H04W 88/02* | (2009.01) |
| *A61B 5/00* | (2006.01) |
| *A61B 5/01* | (2006.01) |
| *A61B 5/04* | (2006.01) |
| *A61B 5/0404* | (2006.01) |
| *A61B 5/0488* | (2006.01) |
| *A61B 5/11* | (2006.01) |
| *G08B 21/02* | (2006.01) |
| *G08B 21/04* | (2006.01) |
| *H04W 4/02* | (2018.01) |
| *H04W 4/90* | (2018.01) |
| *G08B 19/00* | (2006.01) |
| *H04W 4/22* | (2009.01) |

(52) U.S. Cl.
CPC ........ *A61B 5/04012* (2013.01); *A61B 5/0488* (2013.01); *A61B 5/1112* (2013.01); *A61B 5/1118* (2013.01); *A61B 5/681* (2013.01); *A61B 5/6843* (2013.01); *G08B 21/0211* (2013.01); *G08B 21/0286* (2013.01); *G08B 21/043* (2013.01); *G08B 21/0453* (2013.01); *H04W 4/027* (2013.01); *H04W 88/02* (2013.01); *A61B 2562/0219* (2013.01); *G08B 19/00* (2013.01); *G08B 21/0261* (2013.01); *G08B 21/0266* (2013.01); *G08B 21/0269* (2013.01); *G08B 21/0283* (2013.01); *G08B 21/0446* (2013.01); *H04W 4/22* (2013.01); *H04W 4/90* (2018.02)

(58) Field of Classification Search
USPC ................ 340/539.1, 539.11, 539.13, 573.1
See application file for complete search history.

(56) References Cited

FOREIGN PATENT DOCUMENTS

| | | |
|---|---|---|
| CN | 103997713 A | 8/2014 |
| EP | 0915442 A1 | 5/1999 |
| EP | 2463839 A1 | 6/2012 |

OTHER PUBLICATIONS

Machine Translation and Abstract of Chinese Publication No. CN203504628, Mar. 26, 2014, 10 pages.
Foreign Communication From a Counterpart Application, European Application No. 14904124.6, Partial Supplementary European Search Report dated Jul. 28, 2017, 9 pages.
Foreign Communication From a Counterpart Application, PCT Application No. PCT/CN2014/088665, English Translation of International Search Report dated Jul. 17, 2015, 2 pages.
Foreign Communication From a Counterpart Application, PCT Application No. PCT/CN2014/088665, English Translation of Written Opinion dated Jul. 17, 2015, 5 pages.

* cited by examiner

FALL-OFF DETECTION METHOD FOR WEARABLE DEVICE AND WEARABLE DEVICE

CROSS-REFERENCE TO RELATED APPLICATIONS

This application is a national stage of International Application No. PCT/CN2014/088665, filed on Oct. 15, 2014. The aforementioned application is hereby incorporated by reference in its entirety.

TECHNICAL FIELD

Embodiments of the present disclosure relate to the field of information technologies, and in particular, to a fall-off detection method for a wearable device and a wearable device.

BACKGROUND

A wearable device is light and clings to the body of a wearer, and is therefore a suitable medium for communication between the body of the wearer and the world. According to different product forms, wearable devices may be classified into different types such as watches, wristbands, glasses, armbands, and pendants. Nowadays, wearable devices become increasingly popular in people's lives. For example, a child wears a wearable device and a parent can know the whereabouts of the child in time. In some cases, when a wearable device falls off from a wearer, it indicates that the wearer may be in danger. For example, a criminal forcibly removes a wearable device from a child. In such a case, the wearable device cannot recognize whether the wearer is in danger.

SUMMARY

Embodiments of the present disclosure provide a fall-off detection method for a wearable device and a wearable device. After it is detected that a wearable device falls off from a wearer, a scenario mode that the wearer is in can be determined, and an indication can be sent to an external system.

According to a first aspect, a fall-off detection method for a wearable device is disclosed, where the method includes collecting physiological parameter information and activity information of a wearer of the wearable device; when an abnormality is detected in the physiological parameter information of the wearer of the wearable device and a time of the abnormality exceeds a preset time, determining that the wearable device falls off from the wearer; when it is determined that the wearable device falls off from the wearer, determining, according to the collected physiological parameter information and activity information of the wearer of the wearable device, a scenario mode that the wearer is in; and sending, according to the scenario mode that the wearer is in, an indication corresponding to the scenario mode.

With reference to the first aspect, in a first possible implementation manner of the first aspect, the when it is determined that the wearable device falls off from the wearer, determining, according to the collected physiological parameter information and activity information of the wearer of the wearable device, a scenario mode that the wearer is in is, when it is determined that the wearable device falls off from the wearer, determining, according to electrocardiogram signal information of the collected physiological parameter information of the wearer of the wearable device, whether an abnormality exists in the electrocardiogram signal information of the wearer; determining, according to activity area information of the collected activity information of the wearer, whether the wearer is in a preset activity area; and determining, according to the collected electrocardiogram signal information and activity area information of the wearer, the scenario mode that the wearer is in.

With reference to the first aspect, in a second possible implementation manner of the first aspect, the when it is determined that the wearable device falls off from the wearer, determining, according to the collected physiological parameter information and activity information of the wearer of the wearable device, a scenario mode that the wearer is in is, when it is determined that the wearable device falls off from the wearer, determining, according to body temperature signal information and skin resistance signal information of the collected physiological parameter information of the wearer of the wearable device, whether an abnormality exists in the physiological parameter information of the wearer; determining, according to activity area information of the collected activity information of the wearer, whether the wearer is in a preset activity area; and determining, according to the collected body temperature signal information, skin resistance information, and activity area information of the wearer, the scenario mode that the wearer is in.

With reference to the first aspect, in a third possible implementation manner of the first aspect, the when it is determined that the wearable device falls off from the wearer, determining, according to the collected physiological parameter information and activity information of the wearer of the wearable device, a scenario mode that the wearer is in is, when it is determined that the wearable device falls off from the wearer, determining, according to surface electromyography signal (sEMG) information of the collected physiological parameter information of the wearer of the wearable device, acceleration information of the activity information of the wearer of the wearable device, and angular velocity information of the activity information of the wearer of the wearable device, whether an abnormality exists in activity status information of the wearer; determining, according to activity area information of the collected activity information of the wearer, whether the wearer is in a preset activity area of the wearable device; and determining, according to the collected activity status information and activity area information of the wearer, the scenario mode that the wearer is in.

With reference to the first aspect or any possible implementation manner of the first possible implementation manner of the first aspect to the third possible implementation manner of the first aspect, in a fourth possible implementation manner of the first aspect, the scenario mode includes one or more of a scenario mode in which a danger status is low, a scenario mode in which a danger status is high, a scenario mode in which the wearable device is removed normally, or a scenario mode in which the wearable device falls off accidentally.

According to a second aspect, a fall-off detection method for a wearable device is disclosed, where the method includes collecting physiological parameter information and activity information of a wearer of the wearable device; when an interruption abnormality is detected in the physiological parameter information of the wearer of the wearable device and a time of the interruption abnormality exceeds a preset time, determining that the wearable device falls off from the wearer; when it is determined that the wearable device falls off from the wearer, determining, according to the collected activity information of the wearer of the wearable device, a scenario mode that the wearer is in; and sending, according to the scenario mode that the wearer is in, an operation execution indication corresponding to the scenario mode.

With reference to the second aspect, in a first possible implementation manner of the second aspect, where the when it is determined that the wearable device falls off from the wearer, determining, according to the collected activity information of the wearer of the wearable device, a scenario mode that the wearer is in is, when it is determined that the wearable device falls off from the wearer, determining, according to acceleration information of the collected activity information of the wearer of the wearable device and angular velocity information of the activity information of the wearer of the wearable device, whether an abnormality exists in activity status information of the wearer; determining, according to activity area information of the activity information of the wearer, whether the wearer is in a preset activity area; and determining, according to the collected activity status information and activity area information of the wearer, the scenario mode that the wearer is in.

With reference to the second aspect or the first possible implementation manner of the second aspect, in a second possible implementation manner of the second aspect, the scenario mode includes one or more of a scenario mode in which a danger status is low, a scenario mode in which a danger status is high, a scenario mode in which the wearable device is removed normally, or a scenario mode in which the wearable device falls off accidentally.

According to a third aspect, a wearable device is disclosed, where the wearable device includes a first sensor, a second sensor, a processor, a power supply, and a radio frequency circuit, where the processor is in communication connection with the first sensor, the second sensor, and the radio frequency circuit, and the power supply supplies power to the first sensor, the second sensor, the processor, and the radio frequency circuit, where the first sensor is configured to collect physiological parameter information of a wearer of the wearable device; the processor is configured to, when an interruption abnormality in the physiological parameter information of the wearer of the wearable device is detected according to the first sensor and a time of the interruption abnormality exceeds a preset time, determine that the wearable device falls off from the wearer; the second sensor is configured to collect activity information of the wearer of the wearable device; the processor is further configured to, when it is determined that the wearable device falls off from the wearer, determine, according to the physiological parameter information that is collected by the first sensor and that is of the wearer of the wearable device and the activity information that is collected by the second sensor and that is of the wearer of the wearable device, a scenario mode that the wearer is in; and the radio frequency circuit is configured to, under the control of the processor, send, according to the scenario mode that the wearer is in, an operation execution indication corresponding to the scenario mode.

With reference to the third aspect, in a second possible implementation manner of the third aspect, the first sensor includes at least one of an electrocardiogram sensor, a body temperature sensor, a skin resistance sensor, or an electromyography sensor.

With reference to the second possible implementation manner of the third aspect, in a second possible implementation manner of the third aspect, when the first sensor is the electrocardiogram sensor, the second sensor includes either of a global positioning system (GPS) sensor and a Bluetooth® sensor; and the electrocardiogram sensor is configured to collect electrocardiogram signal information of the physiological parameter information of the wearer; and that the processor is further configured to, when it is determined that the wearable device falls off from the wearer, determine, according to the physiological parameter information that is collected by the first sensor and that is of the wearer of the wearable device and the activity information that is collected by the second sensor and that is of the wearer of the wearable device, a scenario mode that the wearer is in is the processor is configured to, when it is determined that the wearable device falls off from the wearer, determine, according to the electrocardiogram signal information of the physiological parameter information that is collected by the electrocardiogram sensor and that is of the wearer, whether an abnormality exists in the electrocardiogram signal information of the wearer; and the processor is further configured to determine, according to activity area information of the activity information that is collected by the GPS sensor or the Bluetooth® sensor and that is of the wearer, whether the wearer is in a preset activity area; and the processor is further configured to determine, according to the electrocardiogram signal information and the activity area information of the wearer, the scenario mode that the wearer is in.

With reference to the second possible implementation manner of the third aspect, in a third possible implementation manner of the third aspect, when the first sensor includes the body temperature sensor and the skin resistance sensor, the second sensor includes either of a GPS sensor and a Bluetooth sensor; the body temperature sensor is configured to collect body temperature signal information of the physiological parameter information of the wearer; and the skin resistance sensor is configured to collect skin resistance signal information of the physiological parameter information of the wearer; and that the processor is further configured to, when it is determined that the wearable device falls off from the wearer, determine, according to the physiological parameter information that is collected by the first sensor and that is of the wearer of the wearable device and the activity information that is collected by the second sensor and that is of the wearer of the wearable device, a scenario mode that the wearer is in is the processor is configured to, when it is determined that the wearable device falls off from the wearer, determine, according to the body temperature signal information that is collected by the body temperature sensor and that is of the wearer and the skin resistance signal information that is collected by the skin resistance sensor and that is of the wearer, whether an abnormality exists in the physiological parameter information of the wearer; and the processor is further configured to determine, according to activity area information of the activity information that is collected by the GPS sensor or the Bluetooth sensor and that is of the wearer, whether the wearer is in a preset activity area; and the processor is further configured to determine, according to the physiological parameter information and the activity area information of the wearer, the scenario mode that the wearer is in.

With reference to the second possible implementation manner of the third aspect, in a fourth possible implementation manner of the third aspect, when the first sensor includes the electromyography sensor, the second sensor includes a triaxial accelerometer sensor and a gyro sensor, and the second sensor further includes either of a GPS sensor and a Bluetooth sensor; and the electromyography sensor is configured to collect sEMG information of the physiological parameter information of the wearer; and that the processor is further configured to, when it is determined that the wearable device falls off from the wearer, determine, according to the physiological parameter information that is collected by the first sensor and that is of the wearer of the wearable device and the activity information that is collected by the second sensor and that is of the wearer of the wearable device, a scenario mode that the wearer is in is the processor is configured to, when it is determined that the wearable device falls off from the wearer, determine activity status information of the activity information of the wearer according to the information collected by the electromyography sensor, the triaxial accelerometer sensor, and the gyro sensor; and the processor is further configured to determine, according to activity area information of the activity information that is collected by the GPS sensor or the Bluetooth sensor and that is of the wearer, whether the wearer is in a preset activity area; and the processor is further configured to determine, according to the activity status information and the activity area information of the wearer, the scenario mode that the wearer is in.

With reference to any possible implementation manner of the first possible implementation manner of the third aspect to the fourth possible implementation manner of the third aspect, in a fifth possible implementation manner of the third aspect, where the scenario mode includes one or more of a scenario mode in which a danger status is low, a scenario mode in which a danger status is high, a scenario mode in which the wearable device is removed normally, or a scenario mode in which the wearable device falls off accidentally.

According to a fourth aspect, a wearable device is disclosed, where the wearable device includes a first sensor, a second sensor, a processor, a power supply, and a radio frequency circuit, where the processor is in communication connection with the first sensor, the second sensor, and the radio frequency circuit, and the power supply supplies power to the first sensor, the second sensor, the processor, and the radio frequency circuit, where the first sensor is configured to collect physiological parameter information of a wearer of the wearable device; the processor is configured to, when an abnormality in the physiological parameter information of the wearer of the wearable device is detected according to the first sensor and a time of the abnormality exceeds a preset time, determine that the wearable device falls off from the wearer; the second sensor is configured to collect activity information of the wearer of the wearable device; the processor is further configured to, when it is determined that the wearable device falls off from the wearer, determine, according to the activity information that is collected by the second sensor and that is of the wearer of the wearable device, a scenario mode that the wearer is in; and the radio frequency circuit is configured to, under the control of the processor, send, according to the scenario mode that the wearer is in, an indication corresponding to the scenario mode.

With reference to the fourth aspect, in a first possible implementation manner of the fourth aspect, when the first sensor is a body temperature sensor, the second sensor includes a triaxial accelerometer sensor and a gyro sensor, and the second sensor further includes either of a GPS sensor and a Bluetooth sensor; and the body temperature sensor is configured to collect body temperature signal information of the physiological parameter information of the wearer; and that the processor is further configured to, when it is determined that the wearable device falls off from the wearer, determine, according to the activity information that is collected by the second sensor and that is of the wearer of the wearable device, a scenario mode that the wearer is in is the processor is further configured to, when it is determined that the wearable device falls off from the wearer, determine, according to activity status information of the activity information that is collected by the triaxial accelerometer sensor and the gyro sensor and that is of the wearer, whether an abnormality exists in the activity status information of the activity information of the wearer; and the processor is further configured to determine, according to activity area information of the activity information that is collected by the GPS sensor or the Bluetooth sensor and that is of the wearer, whether the wearer is located in a preset activity area; and the processor is further configured to determine, according to the activity status information and the activity area information of the wearer, the scenario mode that the wearer is in.

With reference to the fourth aspect or the first possible implementation manner of the fourth aspect, in a second possible implementation manner of the fourth aspect, the scenario mode includes one or more of a scenario mode in which a danger status is low, a scenario mode in which a danger status is high, a scenario mode in which the wearable device is removed normally, or a scenario mode in which the wearable device falls off accidentally.

In the foregoing technical solutions, in the fall-off detection method for a wearable device that is provided in embodiments of the present disclosure, physiological parameter information and activity information of a wearer of the wearable device are collected; when an abnormality is detected in the physiological parameter information of the wearer of the wearable device and a time of the abnormality exceeds a preset time, it is determined that the wearable device falls off from the wearer; when it is determined that the wearable device falls off from the wearer, a scenario mode that the wearer is in is determined according to the collected physiological parameter information and activity information of the wearer of the wearable device; and an indication corresponding to the scenario mode is sent according to the scenario mode that the wearer is in. After it is detected that a wearable device falls off from a wearer, a scenario mode that a wearer is in can be determined, and an indication can be sent to an external system.

BRIEF DESCRIPTION OF DRAWINGS

To describe the technical solutions in the embodiments of the present disclosure more clearly, the following briefly introduces the accompanying drawings required for describing the embodiments. The accompanying drawings in the following description show merely some embodiments of the present disclosure, and a person of ordinary skill in the art may still derive other drawings from these accompanying drawings without creative efforts.

DESCRIPTION OF EMBODIMENTS

To make the objectives, technical solutions, and advantages of the embodiments of the present disclosure clearer, the following clearly describes the technical solutions in the embodiments of the present disclosure with reference to the accompanying drawings in the embodiments of the present disclosure. The described embodiments are a part rather than all of the embodiments of the present disclosure. All other embodiments obtained by a person of ordinary skill in the art based on the embodiments of the present disclosure without creative efforts shall fall within the protection scope of the present disclosure.

Wearable devices in embodiments of the present disclosure include a watch, a wristband, glasses, an armband, and an electronic device that is integrated into clothing, shoes, socks, a helmet, a hat, or the like.

Mood fluctuations of a person can affect physiological parameters such as the pulse and body temperature of the person. For example, nervousness and excitement may quicken the pulse of a person and increase the body temperature of the person. Therefore, mood fluctuations of a person may be determined by monitoring some physiological parameters of the person. To some extent, mood fluctuations of a person can reflect a change of an environment that the person is in. For example, if the heartbeat of a wearer speeds up or the body temperature of a wearer rises or in another case, it indicates that the wearer may be in a dangerous environment.

Figure 1:
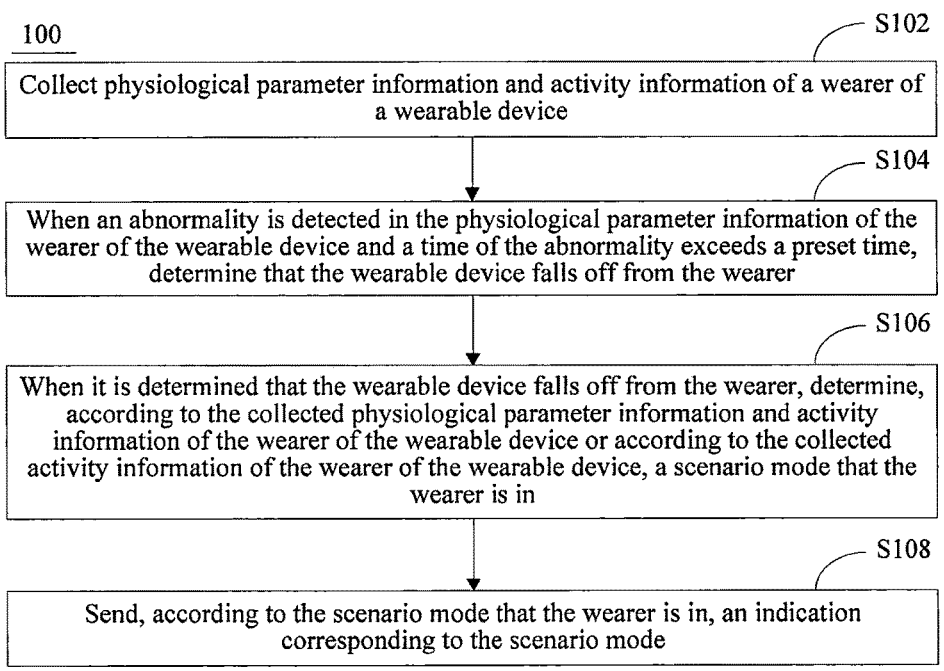
FIG. 1 is a schematic diagram of a fall-off detection method for a wearable device according to an embodiment of the present disclosure.

FIG. 1 provides a schematic diagram of a fall-off detection method for a wearable device according to an embodiment of the present disclosure. The method 100 may be executed by a wearable device, and the method 100 includes the following steps.

S102: Collect physiological parameter information and activity information of a wearer of the wearable device.

The physiological parameter information of the person includes information such as electrocardiogram signal, body temperature, skin resistance, a sEMG, and an electroencephalograph signal (EEG). The electrocardiogram signal information includes information such as a heart rate and sinus beats. The activity information includes activity status information and activity area information.

The electrocardiogram signal information may be collected in real time or at a specified time using an electrocardiogram sensor. The body temperature signal information may be collected in real time or at a specified time using a body temperature sensor. The skin resistance information may be collected in real time or at a specified time using a skin resistance sensor. The sEMG signal information may be collected in real time or at a specified time using an electromyography sensor. By means of analysis of the sEMG signal information of the wearer, arm movement and/or gesture movement information of the activity status information of the wearer can be determined. Acceleration information of the activity status information may be collected in real time or at a specified time using a triaxial accelerometer sensor. Angular velocity information of the activity status information may be collected in real time or at a specified time using a gyro sensor. The activity area information may be collected in real time or at a specified time using a GPS sensor or a Bluetooth sensor. The Bluetooth sensor refers to a device that supports a short range wireless communications technology, and can perform exchange of wireless information between a mobile phone, a palmtop computer, a wireless earphone, a notebook computer, a wearable device, and the like. The Bluetooth sensor may be a Bluetooth chip.

S104: When an abnormality is detected in the physiological parameter information of the wearer of the wearable device and a time of the abnormality exceeds a preset time, determine that the wearable device falls off from the wearer.

The physiological parameter information may be collected using different sensors. Different preset times may be set according to different sensor types. Alternatively, a uniform preset time may be set. For example, the preset time is five seconds. The specific preset time may be set according to an actual need. The abnormality includes a case in which a collected signal is interrupted.

S106: When it is determined that the wearable device falls off from the wearer, determine, according to the collected physiological parameter information and activity information of the wearer of the wearable device or according to the collected activity information of the wearer of the wearable device, a scenario mode that the wearer is in.

The scenario mode that the wearer is in includes one or more of a scenario mode in which a danger status is low, a scenario mode in which a danger status is high, a scenario mode in which the wearable device is removed normally, or a scenario mode in which the wearable device falls off accidentally.

S108: Send, according to the scenario mode that the wearer is in, an indication corresponding to the scenario mode.

The sending, according to the scenario mode that the wearer is in, an indication corresponding to the scenario mode may include the following.

(1) If the wearer is in the scenario mode in which a danger status is high, an emergency call or emergency indication information may be sent to a mobile number that is preset in the wearable device; or emergency indication information may be sent to an alarm or a mobile phone that is paired with the wearable device; or the wearable device may send an indication, for example, the wearable device sends an alarm sound.

(2) If the wearer is in the scenario mode in which a danger status is low, a help request may be sent to a mobile phone that is paired with the wearable device; or a help request may be sent to an alarm that is paired with the wearable device; or the wearable device may send an indication, for example, the wearable device sends an alarm sound.

(3) If the wearer is in the scenario mode in which the wearable device falls off accidentally, accidental fall-off indication information of the wearable device may be sent to a mobile phone that is paired with the wearable device; or accidental fall-off indication information of the wearable device may be sent to an alarm that is paired with the wearable device; or the wearable device may send an indication, for example, the wearable device sends an alarm sound.

(4) If the wearer is in the scenario mode in which the wearable device is removed normally, the wearable device may send no indication information; or may send normal removal indication information.

In the fall-off detection method for a wearable device that is provided in embodiments of the present disclosure, physiological parameter information and activity information of a wearer of the wearable device are collected; when an abnormality is detected in the physiological parameter information of the wearer of the wearable device and a time of the abnormality exceeds a preset time, it is determined that the wearable device falls off from the wearer; when it is determined that the wearable device falls off from the wearer, a scenario mode that the wearer is in is determined according to the collected physiological parameter information and activity information of the wearer of the wearable device or according to the collected activity information of the wearer of the wearable device; and an indication corresponding to the scenario mode is sent according to the scenario mode that the wearer is in. After it is detected that a wearable device falls off from a wearer, a scenario mode that the wearer is in can be determined, and an indication can be sent to an external system.

Figure 2:
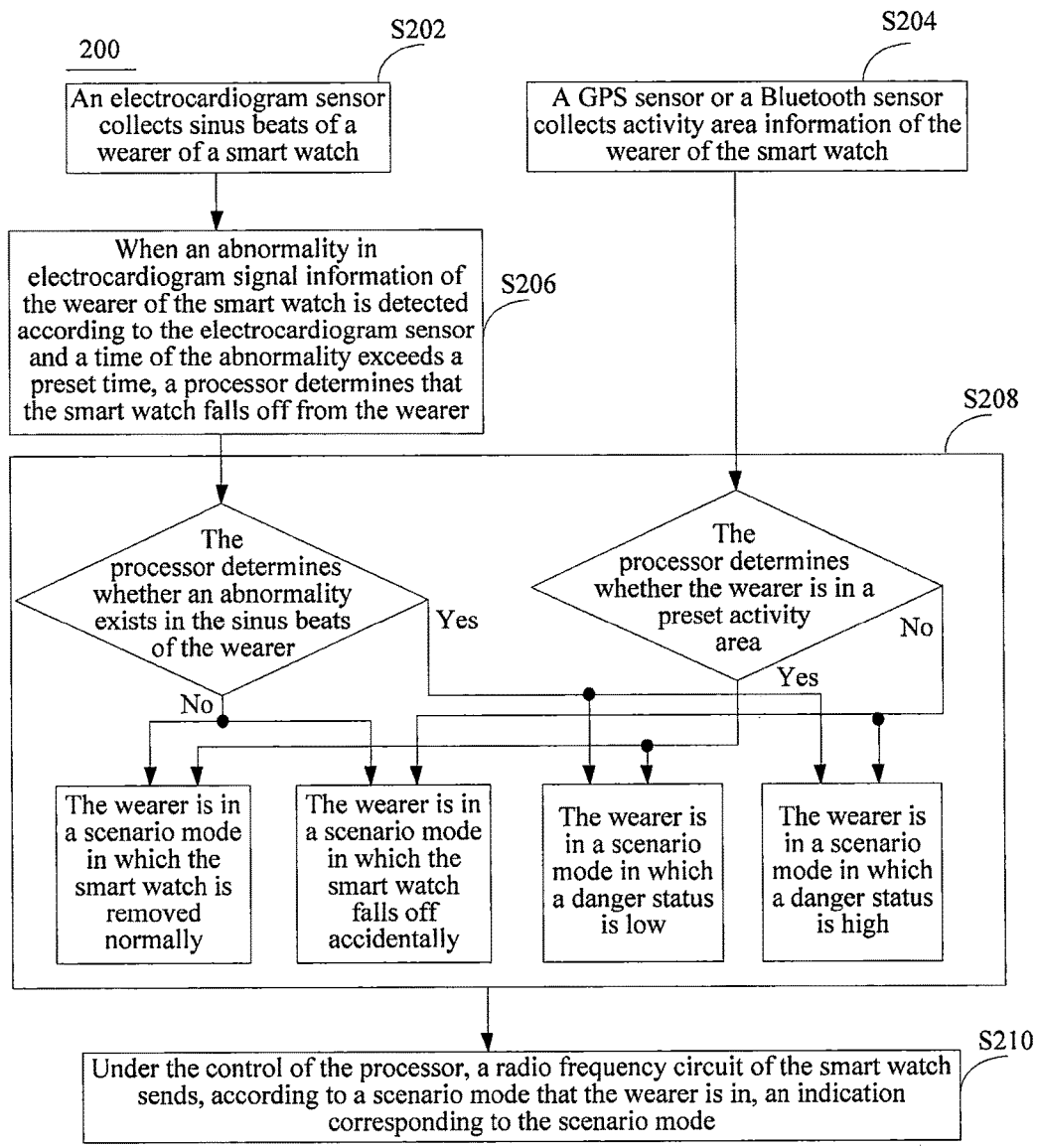
FIG. 2 is a schematic diagram of another fall-off detection method for a wearable device according to an embodiment of the present disclosure.

FIG. 2 provides a schematic diagram of another method 200 for fall-off detection of a wearable device according to an embodiment of the present disclosure. A device for executing the method 200 may be a smart watch, and the smart watch includes a processor, one of an electrocardiogram sensor, a GPS sensor, or a Bluetooth sensor, and a radio frequency circuit. The electrocardiogram sensor is configured to collect electrocardiogram signal information of physiological parameter information of a wearer of the smart watch. The GPS sensor or Bluetooth sensor is configured to collect activity area information of activity information of the wearer. The electrocardiogram sensor may collect information such as a heart rate and sinus beats of the wearer. This embodiment of the present disclosure provides description using an example in which an electrocardiogram sensor collects sinus beats of a wearer.

By means of the method 200 for fall-off detection of a wearable device that is provided in this embodiment of the present disclosure, after it is detected that a wearable device falls off from a wearer, a scenario mode that the wearer is in can be determined, and an indication can be sent to an external system. Specific steps may be as follows.

S202: The electrocardiogram sensor collects sinus beats of the wearer of the smart watch.

The electrocardiogram sensor may collect sinus beat information of electrocardiogram signal information of the wearer in real time or at a specified time. The electrocardiogram signal information is physiological parameter information of the wearer.

S204: The GPS sensor or the Bluetooth sensor collects activity area information of the wearer of the smart watch.

The GPS sensor or Bluetooth sensor may collect the activity area information of the wearer of the smart watch in real time or at a specified time. The activity area information of the wearer refers to a current location of the wearer. For example, the wearer is in a school or the wearer is at home.

S206: When an abnormality in electrocardiogram signal information of the wearer of the smart watch is detected according to the electrocardiogram sensor and a time of the abnormality exceeds a preset time, the processor determines that the smart watch falls off from the wearer.

The preset time may be five seconds. For example, the processor detects that an abnormality exists in the electrocardiogram signal information of the wearer of the smart watch and a time of the abnormality exceeds five seconds. In this case, the processor determines that the smart watch falls off from the wearer. A specific value of the preset time may be determined according to an actual need. The abnormality includes interruption of a collected signal. For example, the electrocardiogram signal information is interrupted for over five seconds.

S208: When it is determined that the smart watch falls off from the wearer, the processor determines, according to sinus beat information that is collected by the electrocardiogram sensor and that is of the wearer, whether an abnormality exists in the sinus beat information of the wearer; and the processor further determines, according to the activity area information that is collected by the GPS sensor or Bluetooth sensor and that is of the wearer, whether an activity area of the wearer is in a preset activity area; and the processor determines, according to the sinus beat information and the activity area information of the wearer, a scenario mode that the wearer is in.

The preset activity area may be a safe activity area of the wearer.

S210: Under the control of the processor of the smart watch, the radio frequency circuit of the smart watch sends, according to the scenario mode that the wearer is in, an indication corresponding to the scenario mode.

In step S208, that the processor determines whether an abnormality exists in the sinus beat information of the wearer includes the following steps.

Step 2081: The processor analyzes the sinus beat information that is detected by the electrocardiogram sensor within a specified time segment before the smart watch falls off from the wearer.

The specified time may be 10 minutes. A specific value of the time segment may be set according to an actual need.

Step 2082: Divide the specified time segment into preset M time segments, where M is a positive integer. For example, the specified time segment is divided into two time segments, where a first time segment is one minute to five minutes, and a second time segment is six minutes to ten minutes. A time interval between every two adjacent sinus beats within the first time segment is calculated, and an average value of the time intervals within the first time segment is then calculated and is recorded as $\bar{t}_1$; and a time interval between every two adjacent sinus beats within the second time segment is calculated, and an average value of the time intervals within the second time segment is then calculated and is recorded as $\bar{t}_2$. A specific quantity M of time segments may be set according to an actual need.

Step 2083: Separately calculate a standard deviation (SD) of time intervals between sinus beats within the M time segments. A calculation formula for the standard deviation is:

$$SD = \sqrt{\frac{\sum_{i=1}^{N}(t_i - \bar{t})^2}{N}}$$

where N is a quantity of sinus beats detected within a corresponding time segment, $t_i$ is a time interval between an $i^{th}$ two adjacent sinus beats within the corresponding time segment, and $\bar{t}$ is an average value of the time interval between sinus beats within the corresponding time segment; a standard deviation of the time intervals between sinus beats within the first time segment is recorded as $x_1$, and a standard deviation of the time intervals between sinus beats within the second time segment is recorded as $x_2$.

Step 2084: Determine whether a change rate of an average value of time intervals between sinus beats within different time segments exceeds a specified average value threshold $\varepsilon_1$. The specified average value threshold $\varepsilon_1$ may be 0.15. The specific specified average value threshold $\varepsilon_1$ may be set according to an actual need. A determining formula is:

$$\frac{|\bar{t}_1 - \bar{t}_2|}{\bar{t}_1} \leq \varepsilon_1$$

Step 2085: Determine whether a change rate of a standard deviation of time intervals between sinus beats within different time segments exceeds a specified standard deviation threshold $\varepsilon_2$. The specified standard deviation threshold $\varepsilon_2$ may be 0.1. The specific specified standard deviation threshold $\varepsilon_2$ may be set according to an actual need. A determining formula is:

$$\frac{|x_1 - x_2|}{x_1} \leq \varepsilon_2$$

If both the change rate of the average value and the change rate of the standard deviation of the time intervals between sinus beats exceed the specified thresholds, it is considered that heart rate variability (HRV) of the wearer changes significantly, that is, an abnormality exists in the sinus beat information of the wearer.

In step S208, that the processor determines whether an activity area of the wearer is in a preset activity area is determining, by the processor according to the activity area information collected by the GPS sensor or Bluetooth sensor, whether the activity area of the wearer is in the preset activity area, where the preset activity area is a safe activity area of the wearer.

In the following cases, the wearer is in the preset activity area.

(1) A current time point is within a time of going to school, and a positioning result of the GPS sensor is that the wearer is in a school.

(2) A current time point is within a dismissing time after school or a time during which the wearer is on the way to school, and a positioning result of the GPS sensor is that the wearer is on a preset path of going to school or leaving school.

(3) At a current time point, a positioning result of the GPS sensor is that the wearer is at home.

(4) The wearable device of the wearer is paired with and is in communication connection with a mobile phone or an alarm of a supervisor. At a current time point, a positioning result of a Bluetooth sensor of the mobile phone or the alarm is that a distance between the wearer and the supervisor does not exceed a specified distance. For example, the specified distance may be 10 meters.

In the following cases, the wearer is in a non-preset activity area.

(1) A current time point is within a time of going to school, and a positioning result of the GPS sensor is that the wearer is in an area outside a school.

(2) A current time point is within a dismissing time after school or a time during which the wearer is on the way to school, and a positioning result of the GPS sensor is that the wearer is in an area outside a preset path of going to school or leaving school.

(3) The wearable device of the wearer pairs with and connects to a mobile phone or an alarm of a supervisor. At a current time point, a positioning result of a Bluetooth sensor of the mobile phone or the alarm is that a distance between the wearer and the supervisor exceeds a specified distance. For example, the specified distance may be 10 meters.

In step S208, that the processor determines, according to the sinus beat information and the activity area information of the wearer, a scenario mode that the wearer is in is may include the following.

(1) By analyzing electrocardiogram signal information of the wearer, the processor of the wearable device finds that within the specified time segment, the change rate of the average value of the time intervals between the sinus beats is 0.19, which is greater than the specified average value threshold $\varepsilon_1=0.15$ and the change rate of the standard deviation of the time intervals between the sinus beats is 0.14, which is greater than the specified standard deviation threshold $\varepsilon_2=0.1$ Therefore, the processor of the smart watch determines that the HRV of the wearer changes significantly. A positioning result of the GPS sensor shows that, when the smart watch falls off, a current location of the wearer does not match a safe activity area corresponding to a current time point. For example, a time point at which the smart watch falls off is within a time of going to school, a safe activity area corresponding to a current time point is a school, and a positioning result of the GPS sensor shows that the wearer is not in the school. Therefore, an abnormality occurs in an activity area of the wearer. With reference to HRV information and activity area information of the wearer, the processor of the smart watch determines that a current scenario mode that the wearer is in is that "the wearer is in the scenario mode in which a danger status is high".

(2) By analyzing electrocardiogram signal information of the wearer, the processor of the wearable device finds that within the specified time segment, the change rate of the average value of the time intervals between the sinus beats is 0.19, which is greater than the specified average value threshold $\varepsilon_1=0.15$ and the change rate of the standard deviation of the time intervals between the sinus beats is 0.14, which is greater than the specified standard deviation threshold $\varepsilon_2=0.1$ Therefore, the processor of the wearable device determines that the HRV of the wearer changes significantly. A positioning result of the GPS sensor shows that, when the smart watch falls off, a current location of the wearer matches a safe activity area corresponding to a current time point. For example, a time point at which the smart watch falls off is within a time of going to school, a safe activity area corresponding to a current time point is a school, and a positioning result of the GPS sensor shows that the wearer is in the school. Therefore, an activity area of the wearer is normal. With reference to HRV information and activity area information of the wearer, the processor of the wearable device determines that a current scenario mode that the wearer is in is that "the wearer is in the scenario mode in which a danger status is low".

(3) By analyzing electrocardiogram signal information of the wearer, the processor of the wearable device finds that within the specified time segment, the change rate of the average value of the time intervals between the sinus beats is 0.09, which is less than the specified average value threshold $\varepsilon_1=0.15$, and the change rate of the standard deviation of the time intervals between the sinus beats is 0.04, which is less than the specified standard deviation threshold $\varepsilon_2=0.1$. Therefore, the processor of the wearable device determines that the HRV of the wearer does not change significantly. A positioning result of the GPS sensor shows that, when the smart watch falls off, a current location of the wearer does not match a safe activity area corresponding to a current time point. For example, a time point at which the smart watch falls off is a dismissing time after school, a safe activity area corresponding to a current time point is a preset path of leaving school for home, and a positioning result of the GPS sensor shows that the wearer is not on the path of leaving school for home. Therefore, an abnormality occurs in an activity area of the wearer. With reference to HRV information and activity area information of the wearer, the processor of the wearable device determines that a current scenario mode that the wearer is in is that "the wearer is in the scenario mode in which the wearable device falls off accidentally".

(4) By analyzing electrocardiogram signal information of the wearer, the processor of the wearable device finds that within the specified time segment, the change rate of the average value of the time intervals between the sinus beats is 0.09, which is less than the specified average value threshold $\varepsilon_1=0.15$, and the change rate of the standard deviation of the time intervals between the sinus beats is 0.04, which is less than the specified standard deviation threshold $\varepsilon_2=0.1$. Therefore, it is considered that the HRV of the wearer does not change significantly. A positioning result of the GPS sensor shows that, when the smart watch falls off, a current location of the wearer matches a safe activity area corresponding to a current time point. For example, a time point at which the smart watch falls off is within a rest time at night, a safe activity area corresponding to a current time point is home, and a positioning result of the GPS sensor shows that the wearer is at home. Therefore, an activity area of the wearer is normal. With reference to HRV information and activity area information of the wearer, the processor of the wearable device determines that a current scenario mode that the wearer is in is that "the wearer is in the scenario mode in which the wearable device is removed normally".

Optionally, that the processor determines, according to the sinus beat information and the activity area information of the wearer, a scenario mode that the wearer is in may also be as follows.

(1) By analyzing electrocardiogram signal information of the wearer, the processor of the wearable device finds that within the specified time segment, the change rate of the average value of the time intervals between the sinus beats is 0.19, which is greater than the specified average value threshold $\varepsilon_1=0.15$, and the change rate of the standard deviation of the time intervals between the sinus beats is 0.14, which is greater than the specified standard deviation threshold $\varepsilon_2=0.1$. Therefore, the processor of the smart watch determines that the HRV of the wearer changes significantly. A positioning result of the GPS sensor shows that, when the smart watch falls off, a current location of the wearer does not match a safe activity area corresponding to a current time point. For example, a time point at which the smart watch falls off is within a time of going to school, a safe activity area corresponding to a current time point is a school, and a positioning result of the GPS sensor shows that the wearer is not in the school. Therefore, an abnormality occurs in an activity area of the wearer. With reference to HRV information and activity area information of the wearer, the processor of the smart watch determines that a current scenario mode that the wearer is in is that "the wearer is in the scenario mode in which a danger status is high".

(2) By analyzing electrocardiogram signal information of the wearer, the processor of the wearable device finds that within the specified time segment, the change rate of the average value of the time intervals between the sinus beats is 0.19, which is greater than the specified average value threshold $\varepsilon_1=0.15$, and the change rate of the standard deviation of the time intervals between the sinus beats is 0.14, which is greater than the specified standard deviation threshold $\varepsilon_2=0.1$. Therefore, the processor of the wearable device determines that the HRV of the wearer changes significantly. A positioning result of the GPS sensor shows that, when the smart watch falls off, a current location of the wearer matches a safe activity area corresponding to a current time point. For example, a time point at which the smart watch falls off is within a time of going to school, a safe activity area corresponding to a current time point is a school, and a positioning result of the GPS sensor shows that the wearer is in the school. Therefore, an activity area of the wearer is normal. With reference to HRV information and activity area information of the wearer, the processor of the wearable device determines that a current scenario mode that the wearer is in is that "the wearer is in the scenario mode in which a danger status is low".

(3) By analyzing electrocardiogram signal information of the wearer, the processor of the wearable device finds that within the specified time segment, the change rate of the average value of the time intervals between the sinus beats is 0.09, which is less than the specified average value threshold $\varepsilon_1=0.15$, and the change rate of the standard deviation of the time intervals between the sinus beats is 0.04, which is less than the specified standard deviation threshold $\varepsilon_2=0.1$. Therefore, the processor of the wearable device determines that the HRV of the wearer does not change significantly. A positioning result of the GPS sensor shows that, when the smart watch falls off, a current location of the wearer does not match a safe activity area corresponding to a current time point. For example, a time point at which the smart watch falls off is a dismissing time after school, a safe activity area corresponding to a current time point is a preset path of leaving school for home, and a positioning result of the GPS sensor shows that the wearer is not on the path of leaving school for home. Therefore, an abnormality occurs in an activity area of the wearer. With reference to HRV information and activity area information of the wearer, the processor of the wearable device determines that a current scenario mode that the wearer is in is that "the wearer is in the scenario mode in which a danger status is low".

(4) By analyzing electrocardiogram signal information of the wearer, the processor of the wearable device finds that within the specified time segment, the change rate of the average value of the time intervals between the sinus beats is 0.09, which is less than the specified average value threshold $\varepsilon_1=0.15$, and the change rate of the standard deviation of the time intervals between the sinus beats is 0.04, which is less than the specified standard deviation threshold $\varepsilon_2=0.1$. Therefore, it is considered that the HRV of the wearer does not change significantly. A positioning result of the GPS sensor shows that, when the smart watch falls off, a current location of the wearer matches a safe activity area corresponding to a current time point. For example, a time point at which the smart watch falls off is within a rest time at night, a safe activity area corresponding to a current time point is home, and a positioning result of the GPS sensor shows that the wearer is at home. Therefore, an activity area of the wearer is normal. With reference to HRV information and activity area information of the wearer, the processor of the wearable device determines that a current scenario mode that the wearer is in is that "the wearer is in the scenario mode in which the wearable device falls off accidentally".

In S210, that under the control of the processor of the smart watch, the radio frequency circuit of the smart watch sends, according to the scenario mode that the wearer is in, an indication corresponding to the scenario mode may include the following.

(1) If the wearer is in the scenario mode in which a danger status is high: the radio frequency circuit of the smart watch may send an emergency call or send emergency indication information to a mobile number that is preset in the wearable device; or the radio frequency circuit of the smart watch may send emergency indication information to an alarm that is paired with the wearable device; or the radio frequency circuit of the smart watch may send a help request to a mobile phone that is paired with the wearable device; or the smart watch may send an indication, for example, the smart watch sends an alarm sound.

(2) If the wearer is in the scenario mode in which a danger status is low: the radio frequency circuit of the smart watch may send a help request to a mobile phone that is paired with the wearable device; or the radio frequency circuit of the smart watch may send a help request to an alarm that is paired with the wearable device; or the smart watch may send an indication, for example, the smart watch sends an alarm sound.

(3) If the wearer is in the scenario mode in which the wearable device falls off accidentally: the radio frequency circuit of the smart watch may send accidental fall-off indication information of the wearable device to a mobile phone that is paired with the wearable device; or the radio frequency circuit of the smart watch may send accidental fall-off indication information of the wearable device to an alarm that is paired with the wearable device; or the smart watch may send an indication, for example, the smart watch sends an alarm sound.

(4) If the wearer is in the scenario mode in which the wearable device is removed normally: the radio frequency circuit of the smart watch may send no indication information; or the radio frequency circuit of the smart watch may send normal removal indication information.

If the electrocardiogram sensor is used to collect heart rate information of the wearer, to determine whether an abnormality exists in the physiological parameter information of the wearer, the solution is similar to that of using the electrocardiogram sensor to collect the sinus beats of the wearer.

By means of the fall-off detection method for a wearable device that is provided in this embodiment of the present disclosure, after it is detected that a smart watch falls off from a wearer, a scenario mode that the wearer is in can be determined, and an indication can be sent to an external system.

Figure 3:
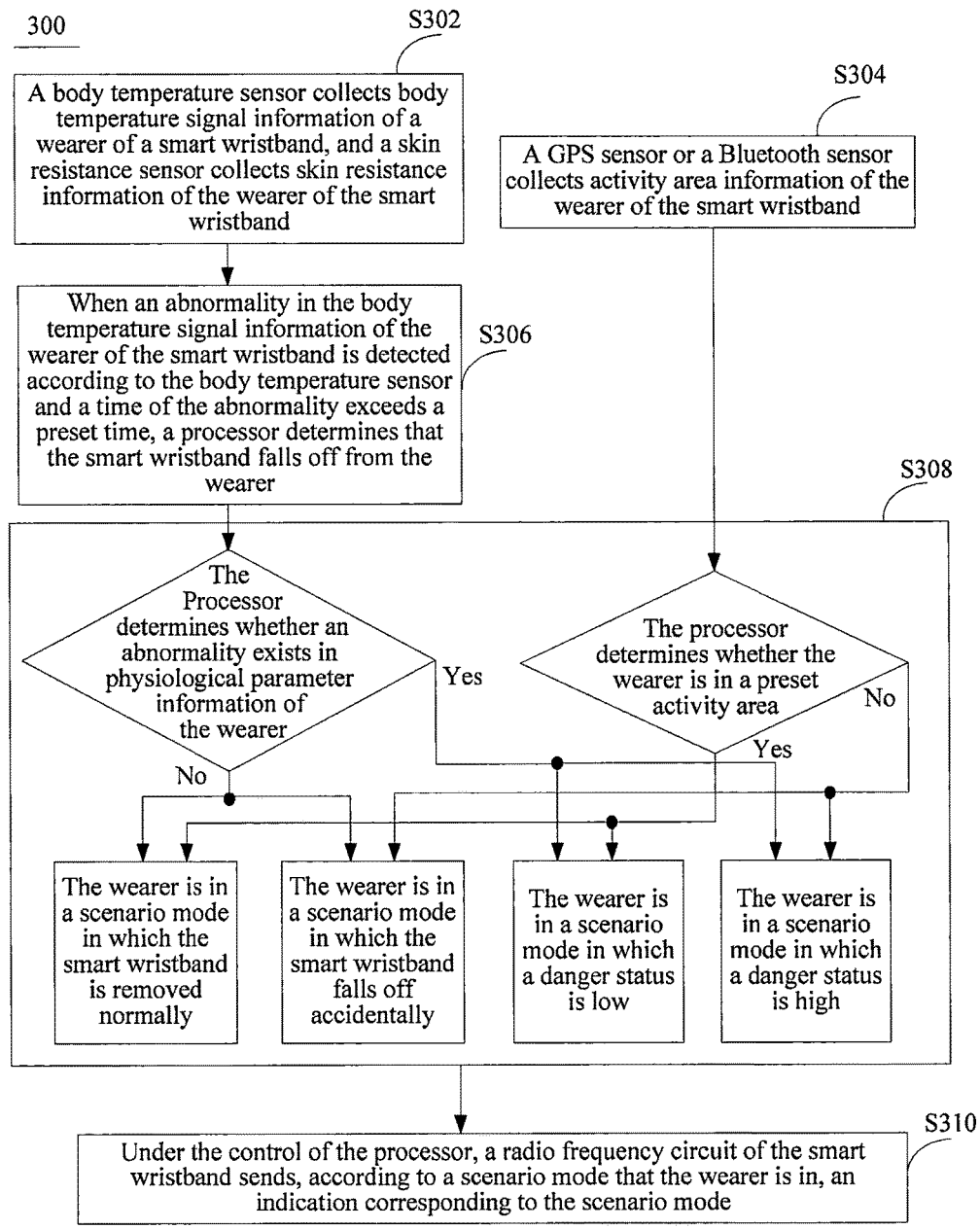
FIG. 3 is a schematic diagram of still another fall-off detection method for a wearable device according to an embodiment of the present disclosure.

FIG. 3 provides still another method 300 for fall-off detection of a wearable device according to an embodiment of the present disclosure. A device for executing the method 300 may be a smart wristband. In the following, the still another fall-off detection method for a wearable device according to an embodiment of the present disclosure is described using a smart wristband as an example.

The smart wristband includes a processor, a first sensor, a second sensor, and a radio frequency circuit. The first sensor of the smart wristband includes a body temperature sensor and a skin resistance sensor. The body temperature sensor is configured to detect body temperature signal information in physiological parameters of a wearer. The skin resistance sensor is configured to detect skin resistance signal information in the physiological parameters of the wearer. The second sensor includes either of a GPS sensor and a Bluetooth sensor. The second sensor is configured to collect activity area information of activity information of the wearer. After it is detected that the smart wristband falls off from the wearer, the smart wristband provided in this embodiment of the present disclosure can determine a scenario mode that the wearer is in, and send an indication to an external system. Specific steps may be the following.

S302: The body temperature sensor collects body temperature signal information of the wearer of the smart wristband, and the skin resistance sensor collects skin resistance information of the wearer of the smart wristband.

The body temperature sensor may collect body temperature signal information of the wearer of the smart wristband in real time or at a specified time. The skin resistance sensor may collect skin resistance information of the wearer of the smart wristband in real time or at a specified time. The body temperature signal information and skin resistance signal information are the physiological parameter information of the wearer.

S304: The GPS sensor or the Bluetooth sensor collects activity area information of the wearer of the smart wristband.

The GPS sensor or Bluetooth sensor may collect the activity area information of the wearer of the smart wristband in real time or at a specified time. The activity area information of the wearer refers to a current location of the wearer. For example, the wearer is in a school, or the wearer is at home.

S306: When an abnormality in the body temperature signal information of the wearer of the smart wristband is detected according to the body temperature sensor and a time of the abnormality exceeds a preset time, the processor determines that the smart wristband falls off from the wearer.

To determine that the smart wristband falls off from the wearer, the processor may use the body temperature sensor to detect that an abnormality exists in a body temperature signal of the wearer and a time of the abnormality exceeds a preset time, for example, three seconds, or detect that a measurement value of a body temperature signal of the wearer is less than a specified body temperature threshold. For example, the specified body temperature threshold is 26° C. Alternatively, to determine that the smart wristband falls off from the wearer, the processor may use the skin resistance sensor at the position to detect that an abnormality exists in a skin resistance signal and a time of the abnormality exceeds a preset time, for example, three seconds, and then the processor determines that the smart wristband falls off from the wearer.

S308: When it is determined that the smart wristband falls off from the wearer, the processor determines, according to the body temperature signal information that is collected by the body temperature sensor and that is of the wearer and the skin resistance signal information that is collected by the skin resistance sensor and that is of the wearer, whether an abnormality exists in physiological parameter information of the wearer; the processor further determines, according to activity area information of the activity information that is collected by the GPS sensor or the Bluetooth sensor and that is of the wearer, whether the wearer is in a preset activity area; and the processor determines, according to the physiological parameter information and the activity area information of the wearer, a scenario mode that the wearer is in.

The preset activity area is a safe activity area of the wearer.

S310: Under the control of the processor of the smart wristband, the radio frequency circuit of the smart wristband sends, according to the scenario mode that the wearer is in, an indication corresponding to the scenario mode.

In step S308, that the processor determines whether an abnormality exists in the physiological parameter information of the wearer includes the following steps.

Step 3081: The processor of the smart wristband analyzes body temperature signals of the wearer that are collected by the body temperature sensor within a specified time segment before the smart wristband falls off from the wearer. Duration of the specified time segment may be two minutes, and specific duration may be determined according to an actual need. For example, the processor of the smart wristband analyzes body temperature signals that are collected by the body temperature sensor within two minutes before the smart wristband falls off from the wearer. An average value of the body temperature signals within the first minute is recorded as $t_1$, and an average value of the body temperature signals within the second minute is recorded as $t_2$. If $|t_1-t_2|<\Delta t$, it is considered that an abnormality occurs in the body temperature signals of the wearer. In this embodiment of the present disclosure, $\Delta t$ may be 0.5° C. A value of $\Delta t$ may be determined according to an actual need.

Step 3082: The processor of the smart wristband analyzes skin resistance signals of the wearer that are collected by the skin resistance sensor within a specified time segment before the smart wristband falls off from the wearer. Duration of the specified time segment may be two minutes, and specific duration of the time segment may be determined according to an actual need. For example, the processor of the smart wristband analyzes skin resistance signals that are collected by the skin resistance sensor within two minutes before the smart wristband falls off from the wearer. The processor of the smart wristband calculates an average value $\Omega$ and an average standard variance $\Delta\Omega$ of the skin resistance signals that are detected within the specified time segment. First, the specified time segment is divided into multiple time windows, and a width of the time window is a preset value. For example, the preset value of the width of the time window is 10 seconds. An average value of the skin resistance signals that are collected within each time window is calculated. If average values of the skin resistance signals collected within three consecutive time windows are all outside of a range $[\Omega-3\times\Delta\Omega, \Omega+3\times\Delta\Omega]$, the processor of the smart wristband determines that an abnormality occurs in the skin resistance signal of the wearer.

If abnormal fluctuations occur in both the body temperature signal and the skin resistance signal of the wearer, it is considered that an abnormal fluctuation occurs in the physiological parameter information of the wearer.

In step S308, the processor determines whether the activity area of the wearer is in the preset activity area. For details, refer to the division of the preset activity area of the smart watch of the wearer in step S208 in the foregoing embodiment of the smart watch.

In step S308, the processor determines, according to the physiological parameter information and the activity area information of the wearer, the scenario mode that the wearer is in. Table 1 shows identification results of the scenario mode.

TABLE 1

Identification results of the scenario mode

| | The wearer is in the preset activity area. | The wearer is in the non-preset activity area. |
|---|---|---|
| The physiological parameter information of the wearer is normal. | The wearer is in the scenario mode in which the wearable device is removed normally. | The wearer is in the scenario mode in which the wearable device falls off accidentally. |
| An abnormality exists in physiological parameter information of the wearer. | The wearer is in the scenario mode in which a danger status is low. | The wearer is in the scenario mode in which a danger status is high. |

Table 2 shows other identification results of the scenario mode.

TABLE 2

Other identification results of the scenario mode

| | The wearer is in the preset activity area. | The wearer is in the non-preset activity area. |
|---|---|---|
| The physiological parameter information of the wearer is normal. | The wearer is in the scenario mode in which the wearable device falls off accidentally. | The wearer is in the scenario mode in which a danger status is low. |
| An abnormality exists in physiological parameter information of the wearer. | The wearer is in the scenario mode in which a danger status is low. | The wearer is in the scenario mode in which a danger status is high. |

In step S310, under the control of the processor of the smart wristband, the radio frequency circuit of the smart wristband is configured to send, according to the scenario mode that the wearer is in, the indication corresponding to the scenario mode. For a specific implementation manner, refer to the description about the sending of the indication corresponding to the scenario mode in step S210 in the foregoing embodiment of the smart watch.

By means of the method 300 provided in this embodiment of the present disclosure, after it is detected that a smart wristband falls off from a wearer, a scenario mode that the wearer is in can be determined, and an indication can be sent to an external system.

Figure 4:
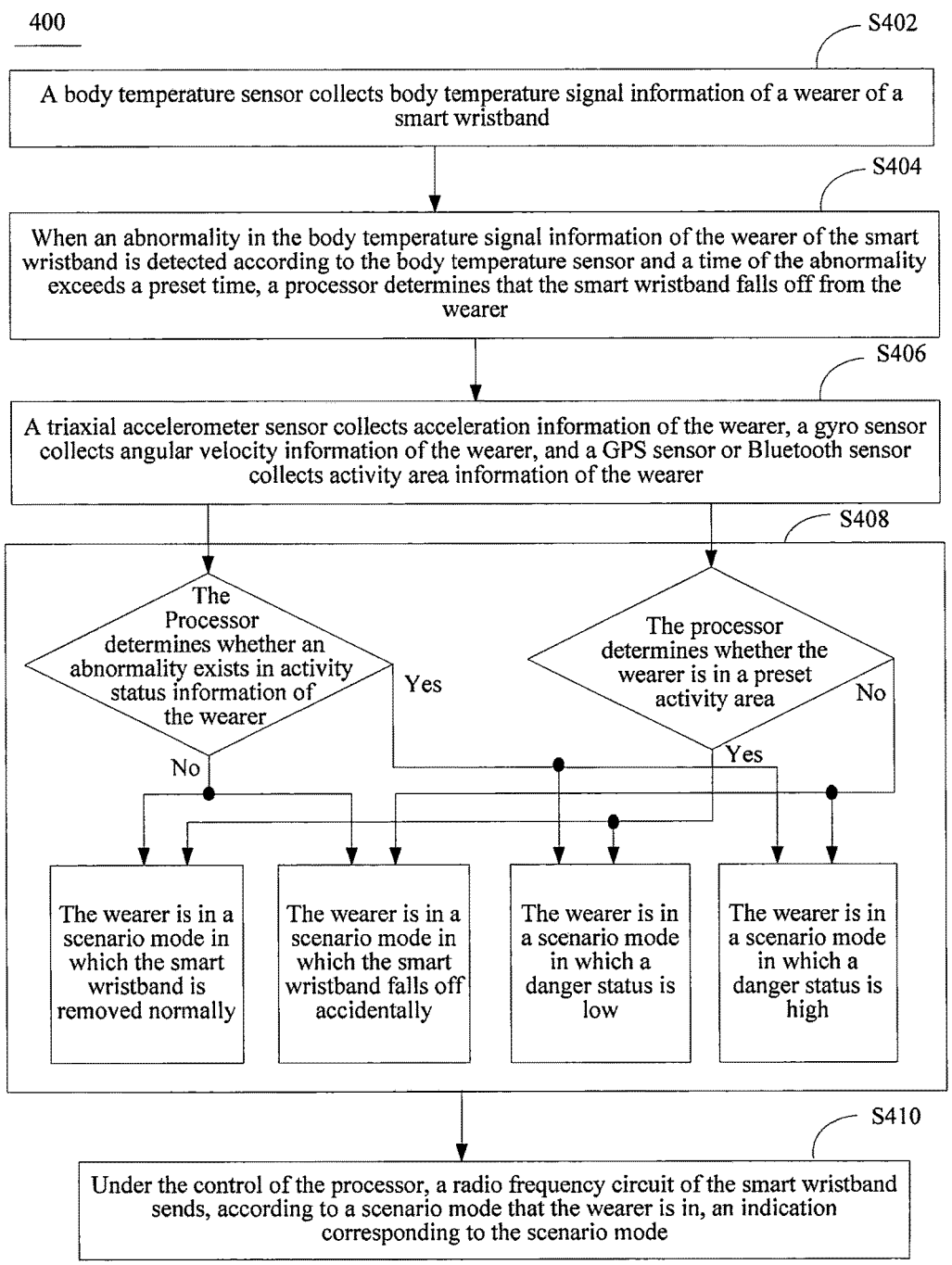
FIG. 4 is a schematic diagram of yet another fall-off detection method for a wearable device according to an embodiment of the present disclosure.

FIG. 4 provides yet another method 400 for fall-off detection of a wearable device according to an embodiment of the present disclosure. A device for executing the method 400 may be another smart wristband.

The smart wristband includes a processor, a first sensor, a second sensor, and a radio frequency circuit. The first sensor of the smart wristband is a body temperature sensor. The body temperature sensor is configured to detect body temperature signal information in physiological parameters of a wearer. The second sensor includes a triaxial accelerometer sensor and a gyro sensor. The second sensor further includes either of a GPS sensor and a Bluetooth sensor. The triaxial accelerometer sensor in the second sensor is configured to collect acceleration information of activity status information of the wearer. The gyro sensor is configured to collect angular velocity information of the activity status information of the wearer. The GPS sensor or Bluetooth sensor in the second sensor is configured to detect activity area information of activity information of the wearer. By means of the method 400 provided in this embodiment of the present disclosure, after it is detected that the smart wristband falls off from the wearer, the scenario mode that the wearer is in can be determined, and an indication can be sent to an external system. Specific steps may be the following.

S402: The body temperature sensor collects body temperature signal information of the wearer of the smart wristband.

The body temperature sensor may collect the body temperature signal information of the wearer of the smart wristband in real time or at a specified time. The body temperature signal information is physiological parameter information of the wearer.

S404: When an abnormality in the body temperature signal information of the wearer of the smart wristband is detected according to the body temperature sensor and a time of the abnormality exceeds a preset time, the processor determines that the smart wristband falls off from the wearer.

The body temperature sensor of the smart wristband detects that an abnormality exists in a body temperature signal of the wearer and a time of the abnormality exceeds a preset time, for example, three seconds; or detects that a measurement value of a body temperature signal of the wearer is less than a specified body temperature threshold. For example, the specified body temperature threshold is 26° Celsius (C). The processor of the smart wristband then determines that the smart wristband falls off from the wearer.

S406: The triaxial accelerometer sensor collects acceleration information of the wearer, the gyro sensor collects angular velocity information of the wearer, and the GPS sensor or Bluetooth sensor collects activity area information of the wearer.

The activity information of the wearer includes the activity status information and the activity area information. The activity status information of the wearer includes the acceleration information that is of the wearer and that is determined by the triaxial accelerometer sensor and the angular velocity information that is of the wearer and that is determined by the gyro sensor.

The triaxial accelerometer sensor may collect the acceleration information in real time or at a specified time. The gyro sensor may collect the angular velocity information of the wearer in real time or at a specified time. The GPS sensor or Bluetooth sensor may collect the activity area information of the wearer in real time or at a specified time.

S408: When it is determined that the smart wristband falls off from the wearer, the processor determines, according to activity status information of the activity information that is collected by the triaxial accelerometer sensor and the gyro sensor and that is of the wearer, whether an abnormality exists in activity status information of the wearer; the processor further determines, according to the activity area information of the activity information that is collected by the GPS sensor or the Bluetooth sensor and that is of the wearer, whether the wearer is in a preset activity area; and the processor determines, according to the activity status information and the activity area information of the wearer, a scenario mode that the wearer is in.

The preset activity area is a safe activity area of the wearer.

S410: Under the control of the processor of the smart wristband, the radio frequency circuit of the smart wristband sends, according to the scenario mode that the wearer is in, an indication corresponding to the scenario mode.

In step S408, the processor determines, according to activity status information of the activity information that is collected by the triaxial accelerometer sensor and the gyro sensor and that is of the wearer, whether an abnormality exists in the activity status information of the wearer, and specific steps may be the following.

Step 4081: The processor of the smart wristband analyzes the acceleration information that is of the wearer and that is collected by the triaxial accelerometer sensor within a specified time segment before the smart wristband falls off. Duration of the specified time segment may be one minute, and specific duration of the time segment may be determined according to an actual need. A resultant acceleration is calculated according to an acceleration measurement value that is on each axis and that is collected by the triaxial accelerometer sensor. A calculation formula is:

$$a = \sqrt{a_x^2 + a_y^2 + a_z^2}$$

where $a_x$ is an acceleration measurement value that is on the x axis and that is of the triaxial accelerometer sensor; $a_y$ is an acceleration measurement value that is on the y axis and that is of the triaxial accelerometer sensor; $a_z$ is an acceleration measurement value that is on the y axis and that is of the triaxial accelerometer sensor; and a is the resultant acceleration.

Step 4082: Compare a resultant acceleration a with a specified acceleration threshold $\varepsilon_a$, and determine whether the resultant acceleration a is greater than the specified acceleration threshold $\varepsilon_a$. The specified acceleration threshold may be $\varepsilon_a = 4.6$ m/s$^2$, and a specific value of the specified acceleration threshold may be set according to an actual need.

Step 4083: Calculate a tilt angle θ of the smart wristband of the wearer, compare the tilt angle θ with a specified tilt angle threshold $\varepsilon_\theta$, and determine whether the tilt angle θ of the smart wristband is greater than the specified tilt angle threshold $\varepsilon_\theta$. The specified tilt angle threshold may be $\varepsilon_\theta = 50°$. The calculation formula for the tilt angle θ is:

$$\theta = \frac{180}{\pi} \cos^{-1}\left(\frac{a}{g}\right)$$

where a is the resultant acceleration that is obtained through calculation in step 4081; g is gravitational acceleration, where g=9.81 m/s$^2$.

Step 4084: The processor of the smart wristband analyzes angular velocity signals of the wearer that are collected by the gyro sensor within a specified time segment before the smart wristband falls off from the wearer. By analyzing information of the angular velocity signals, it is determined whether periodical oscillation exists in the smart wristband.

Step 4085: Combine the analysis results in step 4083 and step 4084, and classify activity statuses of the wearer into a normal activity state and an abnormal activity state. Table 3 describes an activity status determining result.

TABLE 3

Activity status determining result

|  | An acceleration value a is greater than a specified threshold, and the tilt angle θ is greater than a specified threshold. | The acceleration value a is greater than the specified threshold, and the tilt angle θ is less than the specified threshold. | The acceleration value a is less than the specified threshold. |
|---|---|---|---|
| Periodical oscillation exists in an angular velocity signal. | Abnormal activity state | Abnormal activity state | Abnormal activity state |
| Periodical oscillation does not exist in the angular velocity signal. | Abnormal activity state | Normal activity state | Normal activity state |

Step 4086: By analyzing the information collected by the GPS sensor or the Bluetooth sensor, the processor of the smart wristband determines whether the wearer is in the preset activity area. For specific division of the preset activity area, refer to the division of the preset activity area of the smart watch of the wearer in step S208 in the foregoing embodiment of the smart watch. The preset activity area is a safe activity area of the wearer.

In step S408, the processor determines, according to the activity status information and the activity area information of the wearer, the scenario mode that the wearer is in. Table 4 shows identification results of the scenario mode.

TABLE 4

Identification results of the scenario mode

|  | The wearer is in the preset activity area. | The wearer is in the non-preset activity area. |
|---|---|---|
| The activity status of the wearer is normal. | The wearer is in the scenario mode in which the wearable device is removed normally. | The wearer is in the scenario mode in which the wearable device falls off accidentally. |
| An abnormality exists in the activity status of the wearer. | The wearer is in the scenario mode in which a danger status is low. | The wearer is in the scenario mode in which a danger status is high. |

Table 5 shows other identification results of the scenario mode.

TABLE 5

Other identification results of the scenario mode

|  | The wearer is in the preset activity area. | The wearer is in the non-preset activity area. |
|---|---|---|
| The activity status information of the wearer is normal. | The wearer is in the scenario mode in which the wearable device falls off accidentally. | The wearer is in the scenario mode in which a danger status is low. |
| An abnormality exists in activity status information of the wearer. | The wearer is in the scenario mode in which a danger status is low. | The wearer is in the scenario mode in which a danger status is high. |

In step S410, under the control of the processor of the smart wristband, the radio frequency circuit of the smart wristband is configured to send, according to the scenario mode that the wearer is in, the indication corresponding to the scenario mode. For a specific implementation manner, refer to the description about the sending of the indication corresponding to the scenario mode in step S210 in the foregoing embodiment of the smart watch.

By means of the yet another method 400 for fall-off detection of a wearable device that is provided in this embodiment of the present disclosure, after it is detected that the smart watch falls off from a wearer, a scenario mode that the wearer is in can be determined, and an indication can be sent to an external system.

Figure 5:
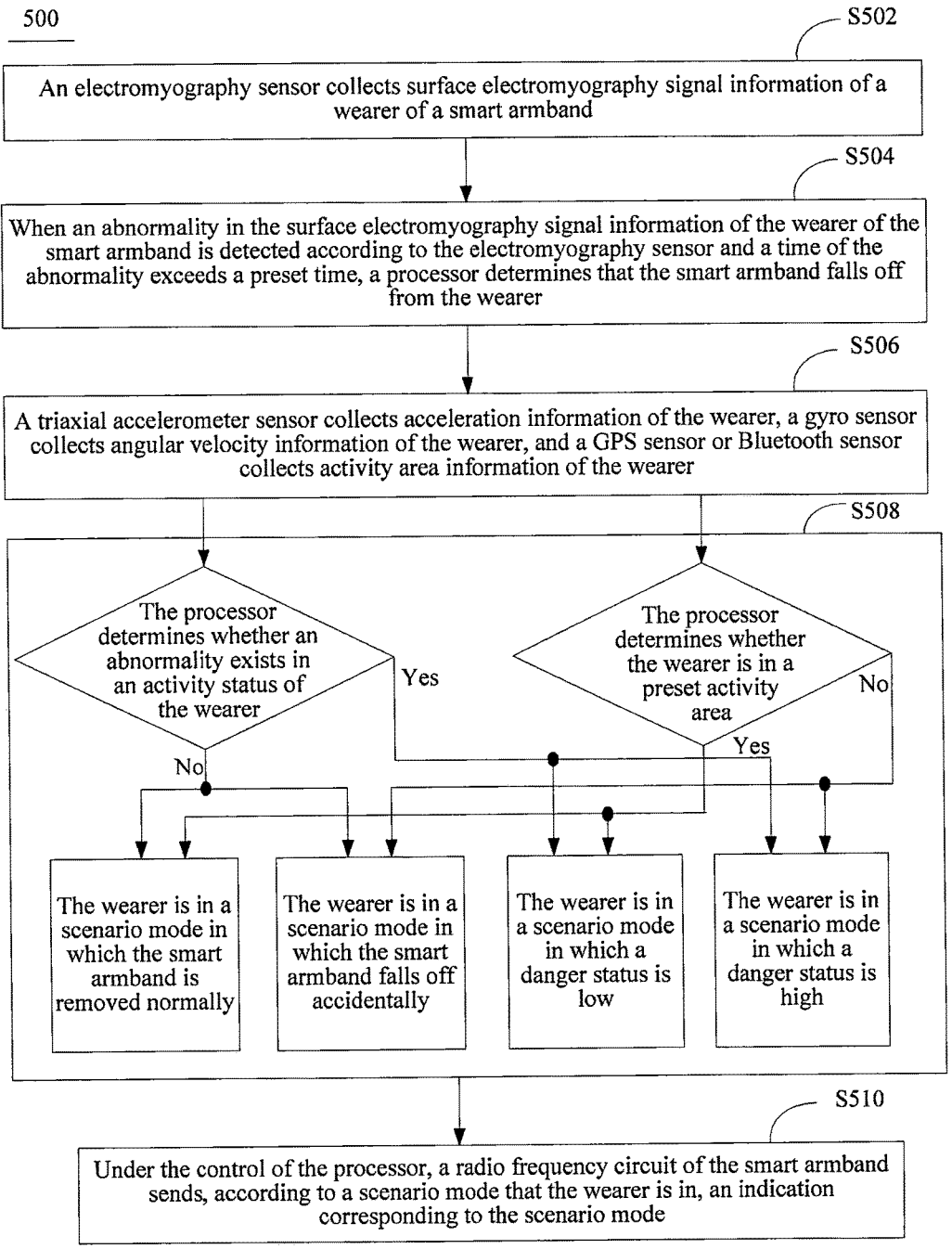
FIG. 5 is a schematic diagram of still yet another fall-off detection method for a wearable device according to an embodiment of the present disclosure.

FIG. 5 provides still yet another method 500 for fall-off detection of a wearable device according to an embodiment of the present disclosure. A device for executing the method 500 may be a smart armband. In the following, the still yet another fall-off detection method for a wearable device provided in this embodiment of the present disclosure is described using the smart armband as an example.

The smart armband includes a processor, a first sensor, a second sensor, and a radio frequency circuit. The first sensor of the smart armband is an electromyography sensor, and is configured to detect a sEMG of the wearer. The second sensor includes a triaxial accelerometer sensor and a gyro sensor. The second sensor further includes either of a GPS sensor and a Bluetooth sensor. The triaxial accelerometer sensor and the gyro sensor in the second sensor are configured to collect activity status information of activity information of the wearer. The GPS sensor and Bluetooth sensor in the second sensor are configured to detect activity area information of the activity information of the wearer.

A physiological basis for recognizing a gesture movement of a wearer using an sEMG signal is that a movement of a specific joint of a limb is controlled by a muscle group corresponding to the movement. An sEMG signal not only can reflect an extension-flexion state and extension-flexion strength of a joint, but also can reflect information about a shape, a location, an orientation, and a movement of a hand in a process in which the person makes a gesture. In addition, a gesture movement including a forearm movement of an upper limb, an elbow joint movement, a wrist joint movement, and a finger movement of an upper limb can be further identified using an sEMG signal collected from a corresponding muscle group. The finger movement further includes a single finger movement and a combined finger movement. For example, the wrist joint movement includes a wrist extension movement, a wrist flexion movement, a palm-up movement, and palm-down movement.

By means of the method 500 for fall-off detection of a wearable device that is provided in this embodiment of the present disclosure, after it is detected that a smart armband falls off from a wearer, a scenario mode that the wearer is in can be determined, and an indication can be sent to an external system. Specific steps may be the following.

S502: An electromyography sensor collects sEMG signal information of the wearer of the smart armband.

The electromyography sensor may collect the sEMG signal information of the wearer of the smart armband in real time or at a specified time. The sEMG signal information is physiological parameter information of the wearer.

S504: When an abnormality in the sEMG signal information of the wearer of the smart armband is detected according to the electromyography sensor and a time of the abnormality exceeds a preset time, the processor determines that the smart armband falls off from the wearer.

The electromyography sensor of the smart armband detects that an abnormality exists in an sEMG signal of the wearer and a time of the abnormality exceeds a preset time, for example, five seconds. In this case, the processor of the smart armband determines that the smart armband falls off from the wearer.

S506: The triaxial accelerometer sensor collects acceleration information of the wearer, the gyro sensor collects angular velocity information of the wearer, and the GPS sensor or Bluetooth sensor collects activity area information of the wearer.

The activity information of the wearer includes the activity status information and the activity area information. The activity status information of the wearer includes gesture movement and/or arm movement information that is of the wearer and that is determined by the electromyography sensor, the acceleration information that is of the wearer and that is determined by the triaxial accelerometer sensor, and the angular velocity information that is of the wearer and that is determined by the gyro sensor.

The triaxial accelerometer sensor may collect the acceleration information in real time or at a specified time. The gyro sensor may collect the angular velocity information of the wearer in real time or at a specified time. The GPS sensor or Bluetooth sensor may collect the activity area information of the wearer in real time or at a specified time.

S508: When it is determined that the smart armband falls off from the wearer, the processor determines, according to the activity status information that is collected by the electromyography sensor, the triaxial accelerometer sensor, and the gyro sensor of the smart armband and that is of the wearer, whether an abnormality exists in an activity status of the wearer; the processor further determines, according to the activity area information that is collected by the GPS sensor or the Bluetooth sensor of the smart armband and that is of the wearer, whether the wearer is in a preset activity area; and the processor determines, according to the activity status information and the activity area information of the wearer, a scenario mode that the wearer is in.

The preset activity area is a safe activity area of the wearer.

S510: Under the control of the processor of the smart armband, the radio frequency circuit of the smart armband sends, according to the scenario mode that the wearer is in, an indication corresponding to the scenario mode.

In step S508, that the processor determines, according to the activity status information of the activity information that is collected by the electromyography sensor, the triaxial accelerometer sensor, and the gyro sensor of the smart armband and that is of the wearer, whether an abnormality exists in the activity status of the wearer may be as follows.

The processor of the smart armband performs pattern recognition on the signal information that is collected by the electromyography sensor, the triaxial accelerometer sensor, and the gyro sensor and that is of the wearer, and compares a result of the pattern recognition with an arm movement and a gesture movement that are preset in the smart armband, to determine whether the result of the pattern recognition matches the preset arm movement and gesture movement. The preset arm movement and gesture movement correspond to different activity statuses of the wearer. If the processor of the smart armband determines that a current arm movement and/or gesture movement successfully matches the preset arm movement and gesture movement, the current activity status of the wearer may be determined. For example, by analyzing signals collected by the electromyography sensor, the triaxial accelerometer sensor, and the gyro sensor, the processor of the smart armband finds that an abnormality may exist in the current arm movement and/or gesture movement of the wearer. By performing pattern recognition on the foregoing collected signals and comparing a result of the pattern recognition with data corresponding to the preset arm movement and gesture movement, the processor determines that the current arm movement and/or gesture movement of the wearer is wrist flexion and backward arm swing, and the processor of the smart armband then determines that an abnormality exists in the current activity status of the wearer.

In step S508, for a specific implementation manner of determining, according to the activity area information of the activity information that is collected by the GPS sensor or the Bluetooth sensor of the smart armband and that is of the wearer, whether the wearer is in the preset activity area, refer to the division of the preset activity area of the smart watch of the wearer in step S208 in the foregoing embodiment of the smart watch. The preset activity area is a safe activity area of the wearer.

In step S508, the processor determines, according to the activity status information and the activity area information of the wearer, the scenario mode that the wearer is in. Table 4 and Table 5 show Identification results of the scenario modes.

In step S510, under the control of the processor of the smart armband, the radio frequency circuit of the smart armband is configured to send, according to the scenario mode that the wearer is in, the indication corresponding to the scenario mode. For a specific implementation manner, refer to the description about the sending of the indication corresponding to the scenario mode in step S210 in the foregoing embodiment of the smart watch.

By means of the further fall-off detection method for a wearable device provided in this embodiment of the present disclosure, after it is detected that a smart armband falls off from a wearer, a scenario mode that the wearer is in can be determined, and an indication can be sent to an external system.

The further fall-off detection method for a wearable device provided in this embodiment of the present disclosure may be executed by a smart headband. The smart headband includes a processor, an electroencephalograph sensor, and a radio frequency circuit. The electroencephalograph sensor is configured to detect an electroencephalograph signal EEG of the wearer.

Step 1: The electroencephalograph sensor collects EEG signal information of the wearer of the smart headband.

The electroencephalograph sensor may collect EEG signal information of the wearer in real time or at a specified time. The EEG signal information is physiological parameter information of the wearer.

Step 2: When an abnormality in an EEG signal of the wearer is detected according to the electroencephalograph sensor and a time of the abnormality exceeds a preset time, the processor determines that the smart headband falls off from the wearer.

The electroencephalograph sensor detects that an abnormality exists in an EEG signal of the wearer and a time of the abnormality exceeds a preset time, for example, five seconds. In this case, the processor of the smart headband determines that the smart headband falls off from the wearer.

Step 3: When it is determined that the smart armband falls off from the wearer, the processor determines, according to the EEG signal information collected by the electroencephalograph sensor of the smart headband, a scenario mode that the wearer is in.

That when it is determined that the smart armband falls off from the wearer, the processor determines, according to the EEG signal information collected by the electroencephalograph sensor of the smart headband, a scenario mode that the wearer is in may include the following steps.

Step 3.1: Extract β wave information from the collected electroencephalograph signal information.

When the wearer feels nervous, anxious, or panicky, the frequency that a β wave appears in the EEG signal surges.

Step 3.2: Analyze features such as an average value, a standard deviation, and average energy of the extracted β wave information of the wearer.

Step 3.3: Establish a classifier according to the features, to recognize the scenario that the wearer is in.

The scenario that the wearer is in includes at least two types: a scenario mode in which the wearer is in a panicky mood and a scenario mode in which the wearer is in a calm mood.

Step 4: Under the control of the processor of the smart headband, the radio frequency circuit of the smart headband sends, according to the scenario mode that the wearer is in, an indication corresponding to the scenario mode.

If the wearer is in the scenario mode in which the wearer is in a panicky mood, an emergency call or emergency indication information may be sent to a mobile number that is preset in the smart headband; or emergency indication information may be sent to an alarm or a mobile phone that is paired with the smart headband; or the smart headband may send an indication, for example, the smart headband sends an alarm sound.

If the wearer is in the scenario mode in which the wearer is in a calm mood, the smart headband may send no indication information; or may send indication information that the wearer is in a calm mood.

Figure 6:
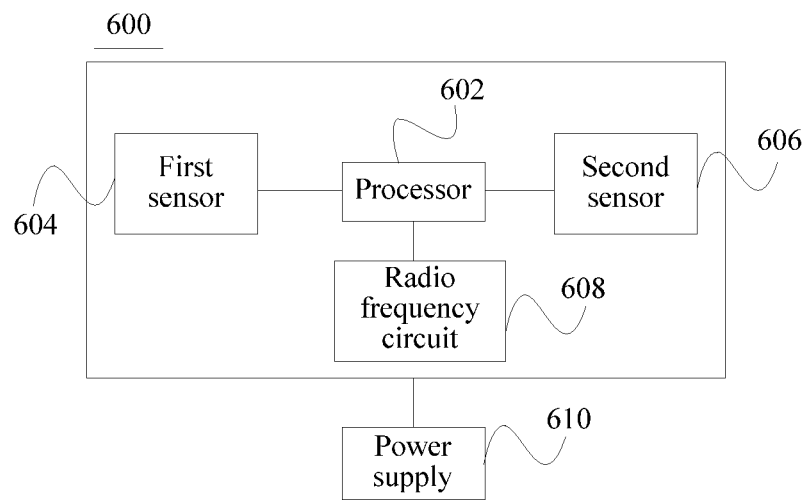
FIG. 6 is a schematic structural diagram of a wearable device according to an embodiment of the present disclosure.

FIG. 6 provides a schematic diagram of a wearable device according to an embodiment of the present disclosure. The wearable device 600 includes a processor 602, a first sensor 604, a second sensor 606, a radio frequency circuit 608, and a power supply 610, where the processor 602 is in communication connection with the first sensor 604, the second sensor 606, and the radio frequency circuit 608; and the power supply 610 supplies power to the first sensor 604, the second sensor 606, the processor 602, and the radio frequency circuit 608.

That the processor 602 is in communication connection with the first sensor 604, the second sensor 606, and the radio frequency circuit 608 refers to that the processor 602 is electrically connected to or connected by means of an input/output bus to the first sensor 604, the second sensor 606, and the radio frequency circuit 608, and the processor 602 can control and communicate with the first sensor 604, the second sensor 606, and the radio frequency circuit 608.

The first sensor 604 is configured to collect physiological parameter information of the wearer of the wearable device.

The processor 602 is configured to, when an abnormality in the physiological parameter information of the wearer of the wearable device is detected according to the first sensor 604 and a time of the abnormality exceeds a preset time, determine that the wearable device falls off from the wearer.

Physiological parameter information of a person includes information such as an electrocardiogram signal, body temperature, and skin resistance, and electrocardiogram signal information of a person includes information such as a heart rate and sinus beats. Different preset times may be set according to different types of the used first sensor 604. Alternatively, a uniform preset time may be set. For example, the preset time is five seconds. The specific preset time may be set according to an actual need.

The second sensor 606 is configured to collect activity information of the wearer of the wearable device.

The processor 602 is further configured to, when it is determined that the wearable device falls off from the wearer, determine, according to the physiological parameter information that is collected by the first sensor 604 and that is of the wearer of the wearable device and the activity information the is collected by the second sensor 606 and that is of the wearer of the wearable device or according to the activity information that is collected by the second sensor 606 and that is of the wearer of the wearable device, a scenario mode that the wearer is in.

The moment when the processor 602 determines that the wearable device falls off from the wearer may refer to a moment when the wearable device falls off from the wearer or may refer to a moment after the wearable device falls off from the wearer.

The activity information of the wearer includes the activity status information and the activity area information. The activity status information refers to a current activity status of the wearer. For example, the wearer is running, the wearer is walking, or the wearer falls. The activity area information refers to a current location of the wearer. For example, the wearer is in a school, or the wearer is at home.

The scenario mode is a scenario mode that is preset in the wearable device, and includes one or more of a scenario mode in which the wearable device is removed normally, a scenario mode in which the wearable device falls off accidentally, a scenario mode in which a danger status is low, or a scenario mode in which a danger status is high.

The radio frequency circuit 608 is configured to, under the control of the processor 602, send, according to the scenario mode that the wearer is in, an indication corresponding to the scenario mode.

That the radio frequency circuit 608 sends, according to the scenario mode that the wearer is in, an indication corresponding to the scenario mode includes the following.

(1) If the wearer is in the scenario mode in which a danger status is high, the radio frequency circuit 608 may send an emergency call or send emergency indication information to a mobile number that is preset in the wearable device; or the radio frequency circuit 608 may send emergency indication information to an alarm or a mobile phone that is paired with the wearable device.

(2) If the wearer is in the scenario mode in which a danger status is low, the radio frequency circuit 608 may send help information to a mobile phone that is paired with the wearable device; or the radio frequency circuit 608 may send help information to an alarm that is paired with the wearable device.

(3) If the wearer is in the scenario mode in which the wearable device falls off accidentally, the radio frequency circuit 608 may send accidental fall-off indication information of the wearable device to a mobile phone that is paired with the wearable device; or the radio frequency circuit 608 may send accidental fall-off indication information of the wearable device to an alarm that is paired with the wearable device.

(4) If the wearer is in the scenario mode in which the wearable device is removed normally, the radio frequency circuit 608 may send no indication information; or the radio frequency circuit 608 may send normal removal indication information.

The wearable device 600 provided in this embodiment of the present disclosure includes a processor 602, a first sensor 604, a second sensor 606, a radio frequency circuit 608, and a power supply 610. The processor 602 is in communication connection with the first sensor 604, the second sensor 606, and the radio frequency circuit 608. The power supply 610 supplies power to the first sensor 604, the second sensor 606, the processor 602, and the radio frequency circuit 608. By means of the wearable device provided in this embodiment of the present disclosure, after it is detected that a wearable device falls off from a wearer, a scenario mode that the wearer is in can be determined, and an indication can be sent to an external system.

The first sensor 604 includes one or more of an electrocardiogram sensor, a body temperature sensor, a skin resistance sensor, or an electromyography sensor. The electrocardiogram sensor may be configured to detect wearer electrocardiogram signal information such as a heart rate and sinus beats. The body temperature sensor may be configured to detect body temperature signal information of the wearer. The skin resistance sensor may be configured to detect skin resistance signal information of the wearer. The electromyography sensor may be configured to detect sEMG information of the wearer. sEMG is an electric signal that accompanies muscle contraction of the wearer. The second sensor 106 includes one or more of a GPS sensor, a Bluetooth sensor, a triaxial accelerometer sensor, or a gyro sensor.

The processor 602 may include an integrated circuit (IC), for example, may include a single packaged IC, or may include multiple packaged ICs that have a same function or different functions and that are connected to one another. For example, a processor unit may include only a central processing unit (CPU), or may be a combination of a digital signal processor (DSP) and a control chip (such as a baseband chip) that is in a communications unit. In an implementation manner of the present disclosure, the CPU may be a single operation core, or may include multiple operation cores.

The radio frequency circuit 608 is configured to receive and send information, and the radio frequency circuit 608 may communicate with a network and another device by means of wireless communication. The wireless communication may use any communications standard or protocol, which includes, but is not limited to, Global System for Mobile communications (GSM), General Packet Radio Service (GPRS), Code Division Multiple Access (CDMA), Wideband Code Division Multiple Access (WCDMA), High Speed Packet Access (HSPA), Evolved High Speed Packet Access (HSPA+), Long Term Evolution (LTE), e-mail, Short Messaging Service (SMS), or the like.

Figure 7A:
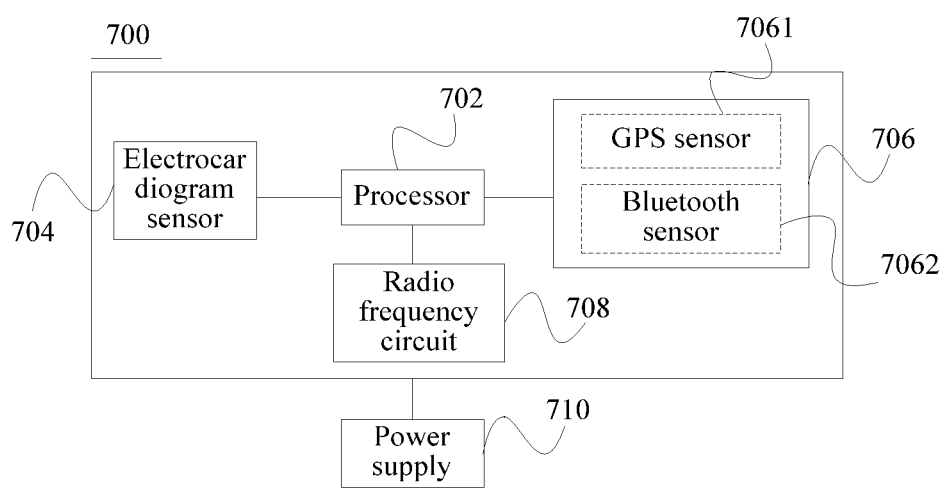
FIG. 7A is a schematic structural diagram of another wearable device according to an embodiment of the present disclosure.

In an embodiment provided in the present disclosure, the wearable device may be a smart watch 700, as shown in FIG. 7A. The smart watch 700 includes a processor 702, an electrocardiogram sensor 704, a second sensor 706, a radio frequency circuit 708, and a power supply 710. The second sensor 706 includes either of a GPS sensor 7061 and a Bluetooth sensor 7062. The processor 702 is in communication connection with the electrocardiogram sensor 704, the second sensor 706, and the radio frequency circuit 708. The power supply 710 supplies power to the processor 702, the electrocardiogram sensor 704, the second sensor 706, and the radio frequency circuit 708.

The electrocardiogram sensor 704 is a first sensor of the smart watch 700, and is configured to collect electrocardiogram signal information of physiological parameter information of the wearer of the smart watch 700. The second sensor 706 of the smart watch includes either of the GPS sensor 7061 and the Bluetooth sensor 7062. The GPS sensor 7061 or the Bluetooth sensor 7062 is configured to collect activity area information of activity information of the wearer. The electrocardiogram sensor may collect information such as a heart rate and sinus beats of the wearer. This embodiment of the present disclosure provides description using an example in which an electrocardiogram sensor collects sinus beats of a wearer.

Figure 7B:
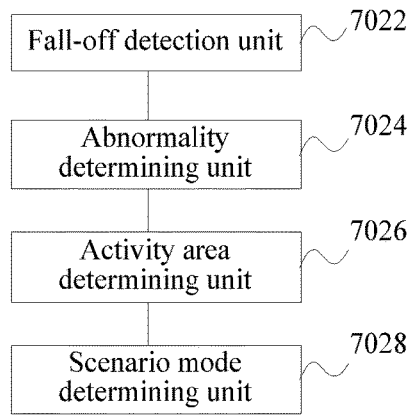
FIG. 7B is a schematic structural diagram of still another wearable device according to an embodiment of the present disclosure.

The processor 702 includes a fall-off detection unit 7022, an abnormality determining unit 7024, an activity area determining unit 7026, and a scenario mode determining unit 7028, as shown in FIG. 7B.

The fall-off detection unit 7022 is configured to, when an abnormality in sinus beat information of the wearer of the smart watch is detected according to the electrocardiogram sensor and a time of the abnormality exceeds a preset time, determine that the smart watch falls off from the wearer.

The preset time may be five seconds. For example, the electrocardiogram sensor detects that an abnormality exists in the sinus beat information of the wearer of the smart watch and the time of the abnormality exceeds five seconds. In this case, the processor determines that the smart watch falls off from the wearer. A specific value of the preset time may be determined according to an actual need.

The abnormality determining unit 7024 is configured to determine whether, according to the sinus beat information that is collected by the electrocardiogram sensor 704 and that is of the wearer, an abnormality exists in the sinus beat information of the wearer. For a specific implementation manner, refer to the step for how to implement that the processor determines whether an abnormality exists in the sinus beat information of the wearer in step S208.

The activity area determining unit 7026 is configured to determine, according to the activity area information that is collected by the GPS sensor 7061 or the Bluetooth sensor 7062 and that is of the wearer, whether an activity area of the wearer is in a preset activity area. The preset activity area is a safe activity area of the wearer. For a specific implementation manner, refer to the division of the preset activity area in step S208.

The scenario mode determining unit 7028 is configured to determine, according to the sinus beat information and the activity area information of the wearer, a scenario mode that the wearer is in. For a specific implementation manner, refer to determining of the scenario mode in step S208.

The radio frequency circuit 708 is configured to, under the control of the processor 702 of the smart watch, send, according to the scenario mode that the wearer is in, an indication corresponding to the scenario mode.

By means of the smart watch provided in this embodiment of the present disclosure, after it is detected that the smart watch falls off from a wearer, a scenario mode that the wearer is in can be determined, and an indication can be sent to an external system.

Figure 8A:
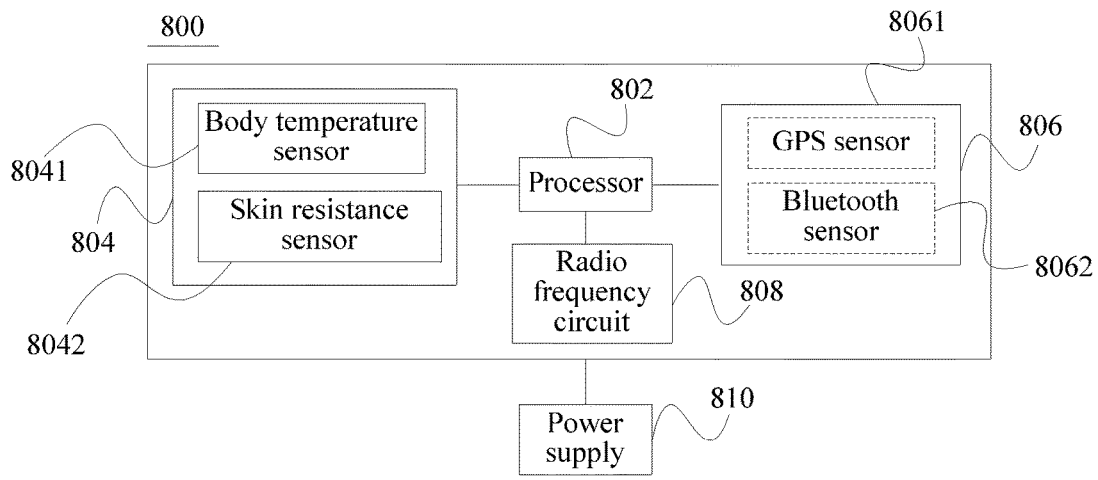
FIG. 8A is a schematic structural diagram of yet another wearable device according to an embodiment of the present disclosure.

In another embodiment provided in embodiments of the present disclosure, the wearable device may be a smart wristband 800, as shown in FIG. 8A. The smart wristband 800 includes a processor 802, a first sensor 804, a second sensor 806, a radio frequency circuit 808, and a power supply 810. The first sensor 804 includes a body temperature sensor 8041 and a skin resistance sensor 8042. The second sensor 806 includes either of a GPS sensor 8061 and a Bluetooth sensor 8062. The processor 802 is in communication connection with the first sensor 804, the second sensor 806, and the radio frequency circuit 808. The power supply 810 supplies power to the processor 802, the first sensor 804, the second sensor 806, and the radio frequency circuit 808.

The body temperature sensor 8041 is configured to detect body temperature signal information in physiological parameters of the wearer. The skin resistance sensor 8042 is configured to detect skin resistance signal information in the physiological parameters of the wearer. The second sensor 806 is configured to collect activity area information of activity information of the wearer.

Figure 8B:
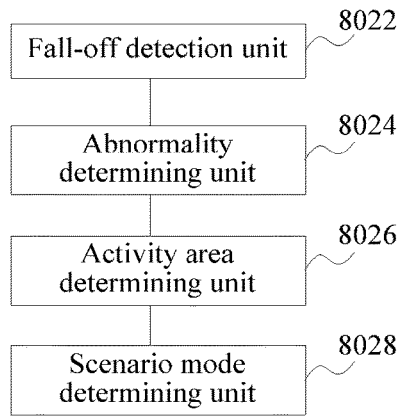
FIG. 8B is a schematic structural diagram of still yet another wearable device according to an embodiment of the present disclosure.

The processor 802 includes a fall-off detection unit 8022, an abnormality determining unit 8024, an activity area determining unit 8026, and a scenario mode determining unit 8028, as shown in FIG. 8B.

The fall-off detection unit 8022 is configured to, when an abnormality in body temperature signal information of the wearer of the smart wristband 800 is detected according to the body temperature sensor 8041 and a time of the abnormality exceeds a preset time, determine that the smart wristband 800 falls off from the wearer. For a specific implementation manner, refer to the foregoing step S306.

The abnormality determining unit 8024 is configured to determine, according to the body temperature signal information that is collected by the body temperature sensor 8041 and that is of the wearer and the skin resistance signal information that is collected by the skin resistance sensor 8042 and that is of the wearer, whether an abnormality exists in physiological parameter information of the wearer. For a specific implementation manner, refer to the foregoing step S308.

The activity area determining unit 8026 is configured to determine, according to the activity area information of the activity information that is collected by the GPS sensor 8061 or the Bluetooth sensor 8062 and that is of the wearer, whether the wearer is in a preset activity area. For a specific implementation manner, refer to the foregoing step S308.

The scenario mode determining unit 8028 is configured to determine, according to the physiological parameter information and the activity area information of the wearer, a scenario mode that the wearer is in. For a specific implementation manner, refer to the foregoing step S308.

The radio frequency circuit 808 is configured to, under the control of the processor 802 of the smart wristband 800, send, according to the scenario mode that the wearer is in, an indication corresponding to the scenario mode.

By means of the smart wristband 800 provided in this embodiment of the present disclosure, after it is detected that the smart wristband 800 falls off from a wearer, a scenario mode that the wearer is in can be determined, and an indication can be sent to an external system.

Figure 9A:
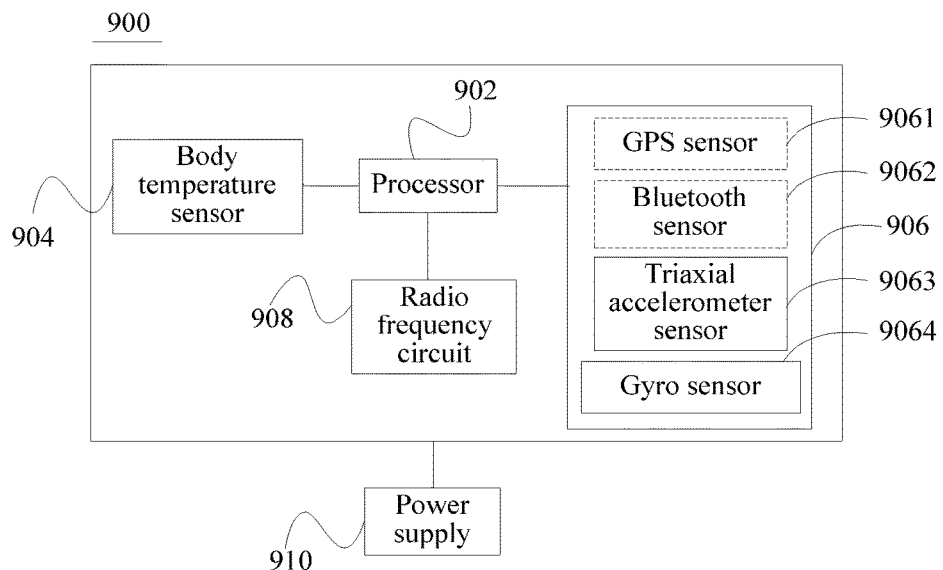
FIG. 9A is a schematic structural diagram of a further wearable device according to an embodiment of the present disclosure.

In still another embodiment provided in the present disclosure, the wearable device may be another smart wristband 900, as shown in FIG. 9A. The smart wristband 900 includes a processor 902, a body temperature sensor 904, a second sensor 906, a radio frequency circuit 908, and a power supply 910. The second sensor 906 includes a triaxial accelerometer sensor 9063 and a gyro sensor 9064. The second sensor 906 further includes either of a GPS sensor 9061 and a Bluetooth sensor 9062. The processor 902 is in communication connection with the body temperature sensor 904, the second sensor 906, and the radio frequency circuit 908. The power supply 910 supplies power to the processor 902, the body temperature sensor 904, the second sensor 906, and the radio frequency circuit 908.

The body temperature sensor 904 is configured to detect body temperature signal information in physiological parameters of the wearer. The triaxial accelerometer sensor 9063 is configured to collect acceleration information of activity information of the wearer. The gyro sensor 9064 is configured to collect angular velocity information of the activity information of the wearer. The GPS sensor 9061 or the Bluetooth sensor 9062 is configured to collect activity area information of the activity information of the wearer.

Figure 9B:
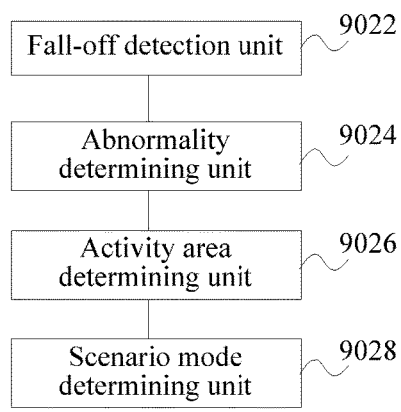
FIG. 9B is a schematic structural diagram of a still further wearable device according to an embodiment of the present disclosure.

The processor 902 includes a fall-off detection unit 9022, an abnormality determining unit 9024, an activity area determining unit 9026, and a scenario mode determining unit 9028, as shown in FIG. 9B.

The fall-off detection unit 9022 is configured to, when an abnormality in the body temperature signal information of the wearer of the smart wristband 900 is detected according to the body temperature sensor 904 and a time of the abnormality exceeds a preset time, determine that the smart wristband 900 falls off from the wearer.

The body temperature sensor 904 of the smart wristband 900 detects that an abnormality exists in a body temperature signal of the wearer and a time of the abnormality exceeds a preset time, for example, three seconds, or detects that a measurement value of a body temperature signal of the wearer is less than a specified body temperature threshold. For example, the specified body temperature threshold is 26° C. In this case, the processor of the smart wristband 900 determines that the smart wristband falls off from the wearer.

The abnormality determining unit 9024 is configured to determine, according to activity status information of the activity information that is collected by the triaxial accelerometer sensor 9063 and the gyro sensor 9064 and that is of the wearer, whether an abnormality exists in the activity status information of the wearer. For a specific implementation manner, refer to the foregoing step S408.

The activity area dividing unit 9026 is configured to determine, according to the activity area information of the activity information that is collected by the GPS sensor 9061 or the Bluetooth sensor 9062 and that is of the wearer, whether the wearer is in a preset activity area. For a specific implementation manner, refer to the foregoing step S408.

The scenario mode determining unit 9028 is configured to determine, according to the activity status information and the activity area information of the wearer, a scenario mode that the wearer is in. For a specific implementation manner, refer to the foregoing step S408.

The radio frequency circuit 908 is configured to, under the control of the processor 902 of the smart wristband 900, send, according to the scenario mode that the wearer is in, an indication corresponding to the scenario mode.

By means of the another smart wristband 900 provided in this embodiment of the present disclosure, after it is detected that the smart wristband 900 falls off from a wearer, a scenario mode that the wearer is in can be determined, and an indication can be sent to an external system.

Figure 10A:
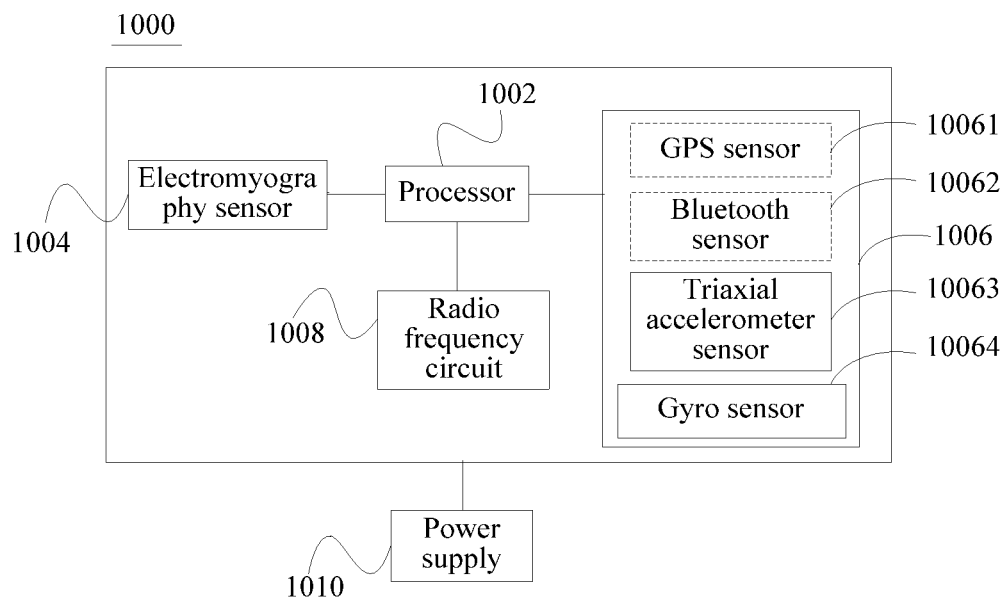
FIG. 10A is a schematic structural diagram of a yet further wearable device according to an embodiment of the present disclosure.

In yet another embodiment provided in embodiments of the present disclosure, the wearable device may be a smart armband 1000, as shown in FIG. 10A. The smart armband 1000 includes a processor 1002, an electromyography sensor 1004, a second sensor 1006, a radio frequency circuit 1008, and a power supply 1010. The second sensor 1006 includes a triaxial accelerometer sensor 10063 and a gyro sensor 10064. The second sensor 1006 further includes either of a GPS sensor 10061 and a Bluetooth sensor 10062. The processor 1002 is in communication connection with the electromyography sensor 1004, the second sensor 1006, and the radio frequency circuit 1008. The power supply 1010 supplies power to the processor 1002, the electromyography sensor 1004, the second sensor 1006, and the radio frequency circuit 1008.

The electromyography sensor 1004 is configured to detect a sEMG of the wearer. The triaxial accelerometer sensor 10063 is configured to collect acceleration information of activity information of the wearer. The gyro sensor 10064 is configured to collect angular velocity information of the activity information of the wearer. The GPS sensor 10061 or the Bluetooth sensor 10062 is configured to collect activity area information of the activity information of the wearer.

Figure 10B:
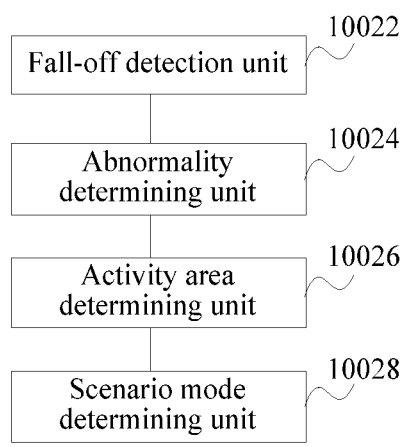
FIG. 10B is a schematic structural diagram of a still yet further wearable device according to an embodiment of the present disclosure.

The processor 1002 includes a fall-off detection unit 10022, an abnormality determining unit 10024, an activity area determining unit 10026, and a scenario mode determining unit 10028, as shown in FIG. 10B.

The fall-off detection unit 10022 is configured to, when an abnormality in sEMG signal information of the wearer of the smart armband 1000 is detected according to the electromyography sensor and a time of the abnormality exceeds a preset time, determine that the smart armband 1000 falls off from the wearer.

The electromyography sensor of the smart armband 1000 detects that an abnormality exists in an sEMG signal of the wearer and a time of the abnormality exceeds a preset time, for example, five seconds. In this case, the processor 1002 of the smart armband 1000 determines that the smart armband 1000 falls off from the wearer.

The abnormality determining unit 10024 is configured to determine, according to the activity status information that is collected by the electromyography sensor 1004, the triaxial accelerometer sensor 10063, and the gyro sensor 10064 of the smart armband 1000 and that is of the wearer, whether an abnormality exists in an activity status of the wearer. For a specific implementation manner, refer to the foregoing step S508.

The activity area determining unit 10026 is configured to determine, according to the activity area information that is collected by the GPS sensor 10061 or the Bluetooth sensor 10062 of the smart armband 1000 and that is of the wearer, whether an activity area of the wearer is in a preset activity area. For a specific implementation manner, refer to the foregoing step S508.

The scenario mode determining unit 10028 is configured to determine, according to the activity status information and the activity area information of the wearer, a scenario mode that the wearer is in. For a specific implementation manner, refer to the foregoing step S508.

The radio frequency circuit 1008 is configured to, under the control of the processor 1002 of the smart armband 1000, send, according to the scenario mode that the wearer is in, an indication corresponding to the scenario mode.

By means of the smart armband 1000 provided in this embodiment of the present disclosure, after it is detected that the smart armband 1000 falls off from a wearer, a scenario mode that the wearer is in can be determined, and an indication can be sent to an external system.

Finally, it should be noted that the foregoing embodiments are merely intended for exemplarily describing the technical solutions of the present disclosure other than limiting the present disclosure. Although the present disclosure and benefits of the present disclosure are described in detail with reference to the foregoing embodiments, persons of ordinary skill in the art should understand that they may still make modifications to the technical solutions described in the foregoing embodiments or make equivalent replacements to some technical features thereof, without departing from the scope of the claims of the present disclosure.

What is claimed is:

1. A fall-off detection method for a wearable device, comprising:
    collecting, via a first sensor of the wearable device, physiological parameter information of the wearable device that relates to a wearer;
    collecting, via a second sensor of the wearable device, activity information of the wearable device that relates to the wearer;
    determining that the wearable device falls off from the wearer when an abnormality is detected in the physiological parameter information of the wearable device that exceeds a preset time;
    determining, based on the physiological parameter information and the activity information, a scenario mode of a plurality of scenario modes of the wearable device when determined that the wearable device falls off from the wearer; and
    sending, based on the scenario mode of the plurality of scenario modes, an indication corresponding to the scenario mode of the plurality of scenario modes for transmission by a radio frequency circuit.

2. The fall-off detection method of claim 1, wherein determining, based on the physiological parameter information and the activity information, the scenario mode of the plurality of scenario modes comprises:
    determining, based on electrocardiogram signal information of the physiological parameter information of the wearer of the wearable device, whether an abnormality exists in the electrocardiogram signal information of the wearer;
    determining, based on activity area information of the activity information, whether the wearable device is located at a preset activity area; and
    determining, based on the electrocardiogram signal information and the activity area information, the scenario mode of the plurality of scenario modes.

3. The fall-off detection method of claim 1, wherein determining, based on the physiological parameter information and the activity information, the scenario mode of the plurality of scenario modes comprises:
    determining, based on body temperature signal information and skin resistance signal information of the physiological parameter information, whether an abnormality exists in the physiological parameter information of the wearer;
    determining, based on activity area information of the activity information, whether the wearable device is at a preset activity area; and
    determining, based on the body temperature signal information, the skin resistance signal information, and the activity area information of the wearer, the scenario mode of the plurality of scenario modes.

4. The fall-off detection method of claim 1, wherein determining, based on the physiological parameter information and the activity information, the scenario mode of the plurality of scenario modes comprises:
    determining, based on surface electromyography signal (sEMG) information of the physiological parameter information, acceleration information of the activity information, and angular velocity information of the activity information, whether an abnormality exists in activity status information of the wearer;

determining, based on activity area information of the activity information, whether the wearable device is at a preset activity area; and determining, based on the activity status information and the activity area information of the wearer, the scenario mode of the plurality of scenario modes.

5. The fall-off detection method of claim 1, wherein the scenario mode of the plurality of scenario modes comprises at least one of:
a scenario mode in which a danger status is low;
a scenario mode in which a danger status is high;
a scenario mode in which the wearable device is removed normally; or
a scenario mode in which the wearable device falls off accidentally.

6. A fall-off detection method for a wearable device, comprising:
collecting, via a first sensor, physiological parameter information;
collecting, via a second sensor, activity information of a wearer of the wearable device;
determining that the wearable device falls off from the wearer when an abnormality is detected in the physiological parameter information of the wearer of the wearable device and a time of the abnormality exceeds a preset time;
determining, based on the collected activity information of the wearer of the wearable device, a scenario mode of the wearable device when determined that the wearable device falls off from the wearer; and
sending, based on the scenario mode of the wearable device, an indication corresponding to the scenario mode for transmission by a radio frequency circuit.

7. The fall-off detection method of claim 6, wherein determining, based on the activity information of the wearable device, the scenario mode of the wearable device comprises:
determining, based on acceleration information of the activity information of the wearable device and angular velocity information of the activity information of the wearable device, whether an abnormality exists in activity status information of the wearable device;
determining, based on activity area information of the activity information of the wearable device, whether the wearable device is at a preset activity area; and
determining, based on the activity status information and activity area information of the wearable device, the scenario mode of the wearable device.

8. The fall-off detection method of claim 6, wherein the scenario mode comprises at least one of:
a scenario mode in which a danger status is low;
a scenario mode in which a danger status is high;
a scenario mode in which the wearable device is removed normally; or
a scenario mode in which the wearable device falls off accidentally.

9. A wearable device, comprising:
a first sensor configured to collect physiological parameter information of a wearer of the wearable device;
a second sensor configured to collect activity information of the wearer of the wearable device;
a radio frequency circuit;
a processor in communication with the first sensor, the second sensor, and the radio frequency circuit; and a power supply configured to supply power to the first sensor, the second sensor, the processor, and the radio frequency circuit, wherein the processor is configured to:
determine that the wearable device falls off from the wearer when an abnormality in the physiological parameter information of the wearer of the wearable device is detected based on the first sensor and a time of the abnormality exceeds a preset time; and
determine, based on the physiological parameter information collected by the first sensor and the activity information collected by the second sensor, a scenario mode of the wearable device when determined that the wearable device falls off from the wearer, and wherein the radio frequency circuit is configured to send, based on the scenario mode of the wearable device, an indication corresponding to the scenario mode.

10. The wearable device of claim 9, wherein the first sensor comprises at least one of an electrocardiogram sensor, a body temperature sensor, a skin resistance sensor, or an electromyography sensor.

11. The wearable device of claim 10, wherein when the first sensor includes the electrocardiogram sensor, the second sensor includes either a global positioning system (GPS) sensor or a Bluetooth® sensor and the electrocardiogram sensor is configured to collect electrocardiogram signal information of the physiological parameter information of the wearer, and wherein the processor is further configured to determine, based on the physiological parameter information collected by the first sensor and the activity information collected by the second sensor, the scenario mode by:
determining, based on the electrocardiogram signal information of the physiological parameter information collected by the electrocardiogram sensor, whether an abnormality exists in the electrocardiogram signal information of the wearer when the wearable device falls off from the wearer; and
determining, based on activity area information of the activity information that is collected by the GPS sensor or the Bluetooth® sensor, whether the wearer is in a preset activity area; and
determining, based on the electrocardiogram signal information and the activity area information of the wearer, the scenario mode of the wearable device.

12. The wearable device of claim 10, wherein when the first sensor comprises the body temperature sensor and the skin resistance sensor, the second sensor comprises either a GPS sensor or a Bluetooth® sensor,
wherein the body temperature sensor is configured to collect body temperature signal information of the physiological parameter information,
wherein the skin resistance sensor is configured to collect skin resistance signal information of the physiological parameter information, and
wherein the processor is further configured to determine, based on the physiological parameter information collected by the first sensor and the activity information collected by the second sensor, the scenario mode by:
determining, based on the body temperature signal information collected by the body temperature sensor and the skin resistance signal information collected by the skin resistance sensor, whether an abnormality exists in the physiological parameter information of the wearer when determined that the wearable device falls off from the wearer;

determining, based on activity area information of the activity information collected by the GPS sensor or the Bluetooth® sensor, whether the wearer is in a preset activity area; and determining, based on the physiological parameter information and the activity area information of the wearer, the scenario mode of the wearable device.

13. The wearable device of claim 10, wherein when the first sensor comprises the electromyography sensor, the second sensor comprises a triaxial accelerometer sensor, a gyro sensor, and either a GPS sensor or a Bluetooth® sensor, wherein the electromyography sensor is configured to collect surface electromyography signal (sEMG) information of the physiological parameter information of the wearer, and wherein the processor is further configured to determine, based on the physiological parameter information collected by the first sensor and the activity information collected by the second sensor, the scenario mode by:

determining activity status information of the activity information of the wearer based on the information collected by the electromyography sensor, the triaxial accelerometer sensor, and the gyro sensor when determined that the wearable device falls off from the wearer;

determining, based on activity area information of the activity information that is collected by the GPS sensor or the Bluetooth® sensor, whether the wearer is in a preset activity area; and determining, based on the activity status information and the activity area information of the wearer, the scenario mode of the wearable device.

14. The wearable device of claim 10, wherein the scenario mode comprises at least one of:

a scenario mode in which a danger status is low;

a scenario mode in which a danger status is high;

a scenario mode in which the wearable device is removed normally; or a scenario mode in which the wearable device falls off accidentally.

* * * * *